United States Patent [19]
Siochi

[11] Patent Number: 6,097,787
[45] Date of Patent: Aug. 1, 2000

[54] SYSTEM AND METHOD FOR CALCULATING SCATTER RADIATION

[75] Inventor: Ramon Alfredo Carvalho Siochi, Fairfield, Calif.

[73] Assignee: Siemens Medical Systems, Inc., Iselin, N.J.

[21] Appl. No.: 09/178,381

[22] Filed: Oct. 23, 1998

Related U.S. Application Data

[60] Provisional application No. 60/095,988, Aug. 10, 1998.

[51] Int. Cl.[7] ........................................ G21K 5/00
[52] U.S. Cl. ................... 378/65; 378/62; 378/69
[58] Field of Search ................. 378/62, 65, 68, 378/69

[56] References Cited

U.S. PATENT DOCUMENTS

| | | | |
|---|---|---|---|
| 3,871,360 | 3/1975 | Van Horn et al. | 600/484 |
| 5,317,616 | 5/1994 | Swerdloff et al. | 378/65 |
| 5,764,723 | 6/1998 | Weinberger et al. | 378/65 |

*Primary Examiner*—David V. Bruce

[57] ABSTRACT

The present invention relates to a fast and accurate method for calculating fluence of a calculation plane over a patient. According to an embodiment of the present invention, only a subset of the collimator leaves are analyzed for the fluence calculation, thus reducing the number of calculations required. Additionally, pre-integrated values of scatter strips, associated with each point of the calculation plane, may be referenced in a lookup table. The use of these pre-integrated values allows the avoidance of adding the fluence contribution of each square on the scattering plane. Rather, pre-calculated values of a subset of the scattering plane (scatter strip) may be referenced and combined, thus reducing the number of calculations required for a final scatter contribution to a point on the calculation plane. Further, the thickness of the collimator leaves is considered in the fluence calculation, thus providing a more accurate model for the scatter contributions of points on the scattering plane.

19 Claims, 24 Drawing Sheets

SYSTEM AND METHOD FOR CALCULATING SCATTER RADIATION

RELATED APPLICATIONS

This application claims priority from U.S. Provisional Patent Application Ser. No. 60/095,988, entitled A FAST METHOD FOR CALCULATING HEAD SCATTER, filed Aug. 10, 1998, which is herein incorporated by reference. This application is related to U.S. patent application Ser. No. 09/178,526, entitled SYSTEM AND METHOD FOR USING PRECALCULATED STRIPS IN CALCULATING SCATTER RADIATION, and to U.S. patent application Ser. No. 09/177,915, entitled SYSTEM AND METHOD FOR CALCULATING SCATTER RADIATION INCLUDING A COLLIMATOR THICKNESS, both being filed concurrently herewith and both of which are also herein incorporated by reference.

FIELD OF THE INVENTION

The invention relates to a radiation emitting device, and more particularly to a system and method for calculating scatter radiation of the radiation emitting device.

BACKGROUND OF THE INVENTION

Radiation emitting devices are generally known and used, for instance, as radiation therapy devices for the treatment of patients. A radiation therapy device usually includes a gantry which can be swiveled around a horizontal axis of rotation in the course of therapeutic treatment. A linear accelerator is typically located in the gantry for generating a high-energy radiation beam for therapy. This high-energy radiation beam can be an electron radiation or photon (x-ray) beam. During treatment, this radiation beam is typically trained on a zone of a patient lying in the isocenter of the gantry rotation.

In order to provide a proper dose of radiation to a patient, a dose chamber may be used. A dose chamber accumulates dose deliveries from the radiation beam. When the dose of the radiation beam reaches a given number of counts, then the radiation beam may be turned off. The unit with which the dose chamber counts is a "monitor unit". Determining how many monitor units to set the dose chamber so that the patient receives a proper dose is typically termed as dosimetry. Once a dose for a patient is determined, this dose typically needs to be translated into monitor units. There may be several factors in translating the dose into monitor units, such as attenuation through the patient, accounting for curvature of patient surface, and accounting of scattered radiation inside the patient.

In determining a dose to a patient, a hypothetical plane, often referred to as a calculation plane, a patient plane, or an isocentric plane, directly above the patient may be used in determining the distribution of radiation intensity over the patient. The unit of measurement for radiation intensity is fluence, which is the number of photons per area per time. This calculation plane over the patient may be divided into squares, herein referred to as calculation squares. In determining the fluence over the calculation plane, only one calculation square above the immediate target is typically calculated for the fluence due to the complication of calculating fluence over all of the squares in the calculation plane.

A problem with calculating the fluence in only one calculation square is that the approximation for the remaining calculation squares may be inaccurate. In particular, in the field of intensity modulation, this type of approximation for fluence of the calculation plane may be wholly inadequate. Intensity modulation typically improves the ratio of radiation dose to critical structures versus dose to target. Improving this ratio is highly desirable since it is assumed that non-target areas are receiving radiation. A common goal is to maximize the radiation dose to a target, such as the tumor, while minimizing the radiation dose to healthy tissue.

Another method for calculating the fluence over the calculation plane attempts to calculate the fluence over each calculation square by using ray tracings through a thin aperture. A potential problem with this conventional calculation is that the volume of ray tracing calculations are typically substantial and a substantial amount of processing power is required. Additionally, a radiation aperture, such as a collimator, typically has enough of a thickness to effect the calculations. Accordingly, calculating with the assumption that the aperture is very thin may result in errors.

It would be desirable to have a method for calculating the fluence over the calculation plane which is fast, efficient, and accurate. The present invention addresses such a need.

SUMMARY OF THE INVENTION

The present invention relates to a fast and accurate method for calculating fluence of a calculation plane over a patient. According to an embodiment of the present invention, only a subset of the collimator leaves are analyzed for the fluence calculation, thus reducing the number of calculations required. Additionally, pre-integrated values of scatter strips, associated with each point of the calculation plane, may be referenced in a lookup table. The use of these pre-integrated values allows the avoidance of adding the fluence contribution of each square on the scattering plane. Rather, pre-calculated values of a subset of the scattering plane (scatter strip) may be referenced and combined, thus reducing the number of calculations required for a final scatter contribution to a point on the calculation plane. Further, the thickness of the collimator leaves is considered in the fluence calculation, thus providing a more accurate model for the scatter contributions of points on the scattering plane.

According to an embodiment of the present invention, for each square (herein referred to as a point) on the calculation plane, a subset of collimator leaves which may affect fluence calculation is determined. In addition, scatter strips in the scattering plane associated with the analyzed point on the calculation plane is determined. For every line that can be traced from the calculation point to each scatter strip, it is determined which leaves intersect the traced line on the bottom of the leaf and which leaves intersect the traced line on the top of the leaf, thus taking into consideration the thickness of the leaves within the determined subset of the leaves. Pre-integrated values of the scatter strips may then be referenced in a lookup table to assist in the performance of the fluence calculation over each calculation point in the calculation plane.

A method according to an embodiment of the present invention for calculating scatter radiation is presented. The method comprises providing a scattering plane, wherein the scattering plane is divided into a plurality of sections. A scatter strip associated with the scattering plane is determined, wherein the scatter strip contains at least two of the plurality of sections. A fluence value associated with the scatter strip is also determined.

A system according to an embodiment of the present invention for calculating scatter radiation is also presented. The system comprises a processor configured to provide a scattering plane, wherein the scattering plane is divided into a plurality of sections. The processor is also configured to determine a scatter strip associated with the scattering plane, wherein the scatter strip contains at least two of the plurality of sections. The processor is further configured to determine a fluence value associated with the scatter strip. A memory is coupled with the processor, wherein the memory is configured to provide the processor with instructions.

Another method according to an embodiment for calculating scatter radiation is also provided. The method comprises determining a scatter strip associated with a scattering plane; determining a subset of collimator leaves; and calculating fluence, wherein the fluence calculation is related to the scatter strip and the subset of collimator leaves.

Another system according to an embodiment of the present invention for calculating scatter radiation is also presented. The system comprises a processor configured to determine a scatter strip associated with a scattering plane, determine a subset of collimator leaves and calculate fluence, wherein the fluence calculation is related to the scatter strip and the subset of collimator leaves. The system also includes a memory coupled to the processor, the memory being configured to provide the processor with instructions.

In another aspect of the invention, a method according to an embodiment of the present invention for calculating scatter radiation is presented. The method comprises providing a collimator leaf position and determining a subset of collimator leaves. The method also calculates fluence, wherein the fluence calculation is related to the subset of collimator leaves.

A system according to an embodiment of the present invention for calculating scatter radiation is also presented. The system comprises a memory configured to provide a collimator leaf position and a processor coupled to the memory. The processor is configured to determine a subset of collimator leaves, and is also configured to calculate fluence, wherein the fluence calculation is related to the subset of collimator leaves.

Another method according to an embodiment of the present invention for calculating scatter radiation is presented. The method comprises determining whether a ray traced from a calculation point to a portion of a scattering plane intersects a first portion of a collimator leaf or a second portion of the collimator leaf. The method also calculates fluence, wherein the fluence calculation is related to a first intersection, if the ray intersects the first portion; and wherein the fluence calculation is related to a second intersection, if the ray intersects the second portion.

Yet another system according to an embodiment of the present invention for calculating scatter radiation is presented. The system comprises a processor configured to determine whether a ray traced from a calculation point to a portion of a scattering plane intersects a first portion of a collimator leaf or a second portion of the collimator leaf; the processor also being configured to calculate fluence, wherein the fluence calculation is related to a first intersection, if the ray intersects the first portion; and wherein the fluence calculation is related to a second intersection, if the ray intersects the second portion. A memory is coupled with the processor, the memory being configured to provide the processor with instructions.

DETAILED DESCRIPTION OF THE PREFERRED EMBODIMENTS

The following description is presented to enable one of ordinary skill in the art to make and to use the invention and is provided in the context of a patent application and its requirements. Various modifications to the preferred embodiments will be readily apparent to those skilled in the art and the generic principles herein may be applied to other embodiments. Thus, the present invention is not intended to be limited to the embodiment shown but is to be accorded the widest scope consistent with the principles and features described herein.

Figure 1:
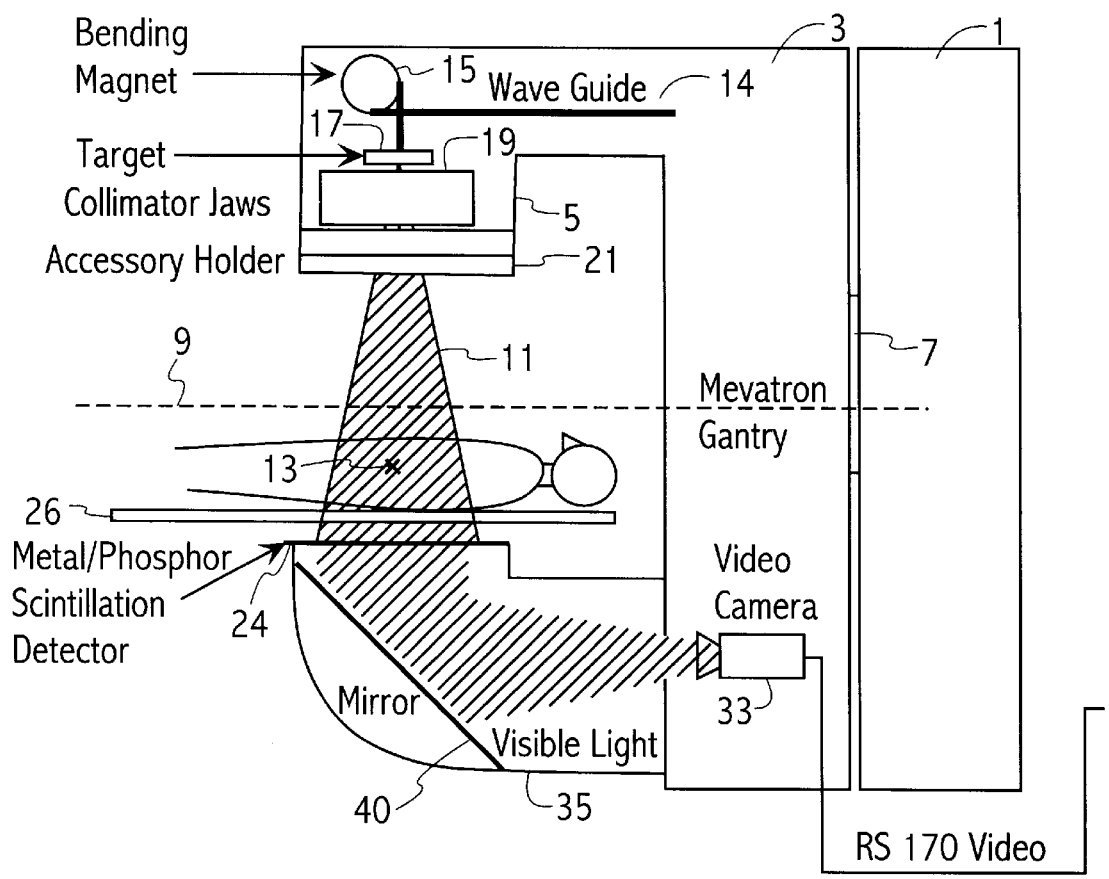
FIG. 1 is an illustration of a radiation emitting apparatus suitable for implementing an embodiment of the present invention.

FIG. 1 is a schematic diagram of an example of a linear accelerator treatment device suitable for implementing an embodiment of the present invention. FIG. 1 shows a linear accelerator device with a stand 1 which is typically anchored firmly to the floor. Stand 1 supports a gantry 3 including a treatment head 5. Gantry 3 can be rotated on bearing 7 around a horizontal axis 9. Within gantry 3 and treatment head 5 are shown to include a waveguide 14 which accelerates electrons. Waveguide 14 is shown to be coupled with a bending magnet 15 which directs the electron beam through target 17 and into collimator 19. The resulting beam may also optionally be radiated through some type of accessory in the accessory holder 21.

In stand 1, an electron injector is typically provided which supplies injector pulses to an electron gun arranged in gantry 3. Electrons are emitted from the electron gun into waveguide 14 to. be accelerated. An electromagnetic field supplied to waveguide 14 typically accelerates the electrons emitted by the electron gun for forming an electron beam. In treatment head 5, the electron beam typically enters an evacuated envelope which bends the electron beam, for example, by 270 degrees. The electron beam then typically leaves the envelope through a window. If electron radiation is to be generated, a scattering foil is typically moved into the trajectory of the electron beam. If x-ray radiation is to be generated, a target is typically moved into the trajectory. The current of the electron beam is caused to be higher than during the generation of the electron radiation because more current is necessary for generating x-ray radiation due to deceleration of the electrons in the target. The x-rays are typically of penetrating power and may be used for the treatment of deep seated tumors, whereas the electrons themselves may be used directly to treat more superficial cancers. During treatment, the patient rests on a treatment couch 26 and intersects the treatment area at an isocenter 13.

Optionally, at a front surface of the side of gantry 3, a retractable and collapsible portal imaging detector housing 35 allows radiation treatment to be performed simultaneously with visualization of the patient's anatomy within the x-ray radiation beam. After passing through the patient's body, the x-rays impinge upon image detector 24, is reflected off mirror 40, and captured by a video camera 33. The video camera may be coupled with an integrated treatment work station wherein the functions and control of the video camera may be controlled in the same system as the functions and control of gantry 3 adjustments. Alternatively, video camera 33 may be coupled with a computer system which may be electronically accessible by another computer system, wherein the second computer system controls the motions and adjustments of gantry 3. Yet another alternative is for video camera 33 to be coupled to a video camera computer system while the motions and control of gantry 3 are coupled to a separate computer system.

Figure 2:
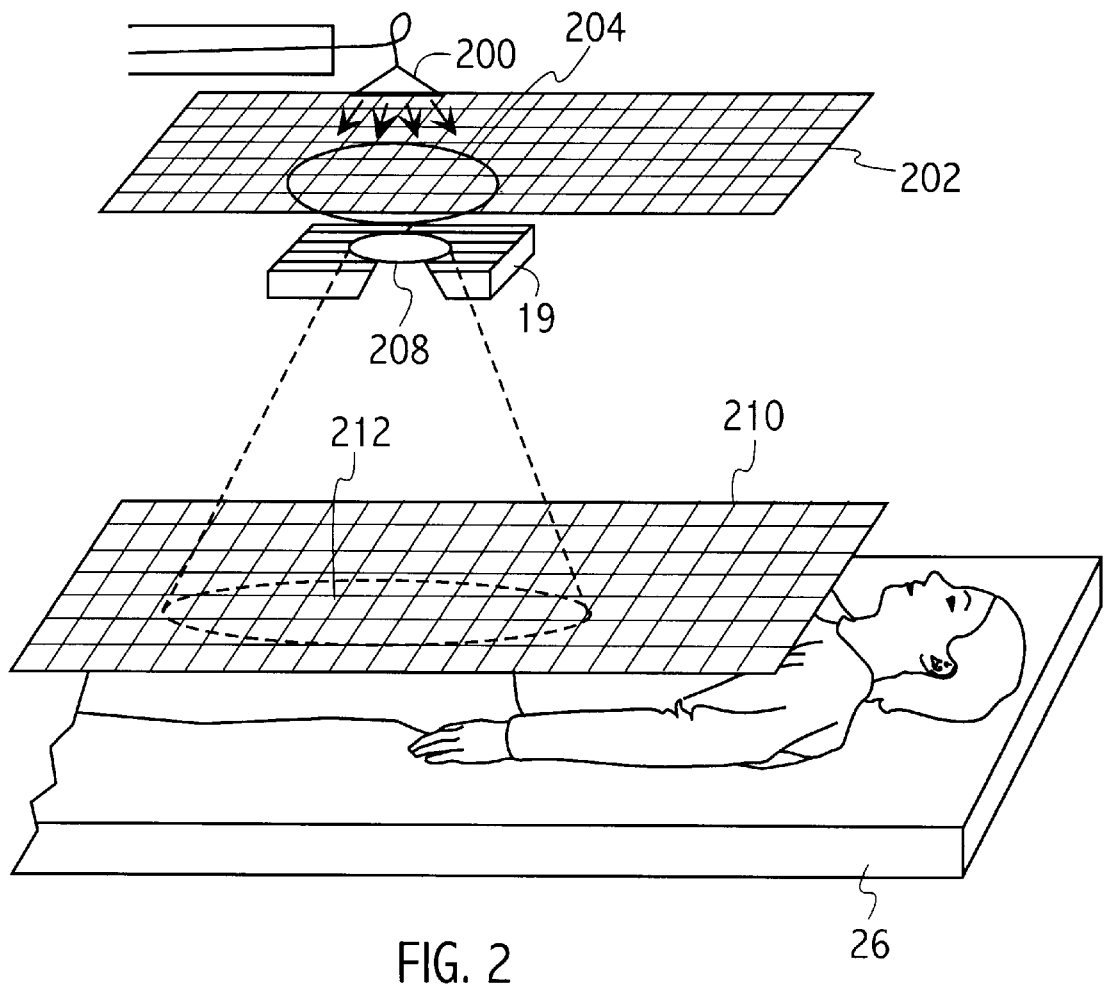
FIG. 2 is an illustration of the radiation beam flowing through a scattering plane and a calculation plane.

FIG. 2 is an illustration of a radiation beam flowing through the hypothetical constructs of a scattering plane 202 and a calculation plane 210. The diagram of FIG. 2 shows a patient lying upon a patient table 26 with a radiation beam flowing through a flattening filter 200 above the patient. The primary function of the flattening filter 200 is to encourage the radiation intensity to be uniform over the field. Once the radiation beam flows through the flattening filter 200, there are primary rays of the radiation beam, which flow radially down from the target and down to the patient. In addition to the primary rays, some rays are scattered in various directions. Some of these scattering rays will bounce off objects and eventually reach the patient. In determining the fluence over the patient, the contributions from both the primary rays and the scattering rays need to be considered.

Once the radiation beam flows through the flattening filter 200, the rays flow through a dose chamber 204. After the dose chamber, the radiation beam flows through a collimator 19 through a collimator aperture 208 and on to the patient. A hypothetical construct, herein referred to as a scattering plane 202, is situated between the flattening filter 200 and the dose chamber 204. The scattering plane 202 is typically divided into a plurality of squares. Each square in the scattering plane 202 may be considered a source of radiation. Each scatter source can give a scatter element $\Delta$ s, wherein $\Delta s \approx Ae^{(-br)}$, wherein s is the scatter element, A is amplitude, e is the exponential function, b is an attenuation coefficient, and r is the radial distance from a central axis of the radiation beam. Other functions may be suitable, and while the current embodiment uses the exponential function, the method is not limited to using the exponential function; a Gaussian or any other radially symmetric function that decreases with radial distance and which can fit the experimental data can be used. The central axis is a line flowing straight through the center of the flattening filter 200. According to this approximation, the scattering source intensity diminishes exponentially as the source location moves away from the central axis. For further information regarding modeling radiation beams using a scattering plane, one may refer to *Head Scatter Modeling for Irregular Field Shaping and Beam Intensity Modulation*, by Hounsell & Wilkinson, PHYS. MED. BIOL. 42 (1997) 1739–1747, IOP Publishing Ltd.

Another hypothetical construct, a calculation plane 210 (sometimes referred to as a patient plane, or an isocentric plane) may also be thought of as being positioned directly above the patient. The calculation plane 210 is also typically divided into squares. When a radiation beam, such as an x-ray beam, reaches a patient, it will cover an area 212 of the calculation plane 210. The area 212 covered by the radiation beam onto the calculation plane 210 is the area that a fluence calculation is performed. Calculation points discussed herein refers to calculation points within the area 212 covered by the radiation beam. As previously mentioned, fluence describes the distribution of radiation intensity and is defined as the number of photons per area per time.

Figure 3A:
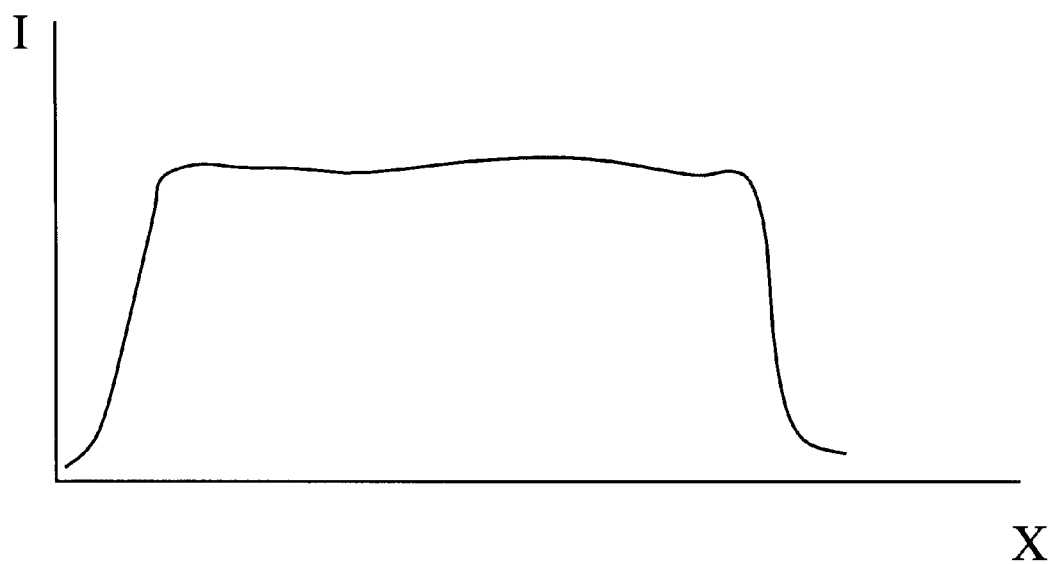
FIGS. 3A–3B show graphs of radiation intensity over the calculation plane.
Figure 3B:
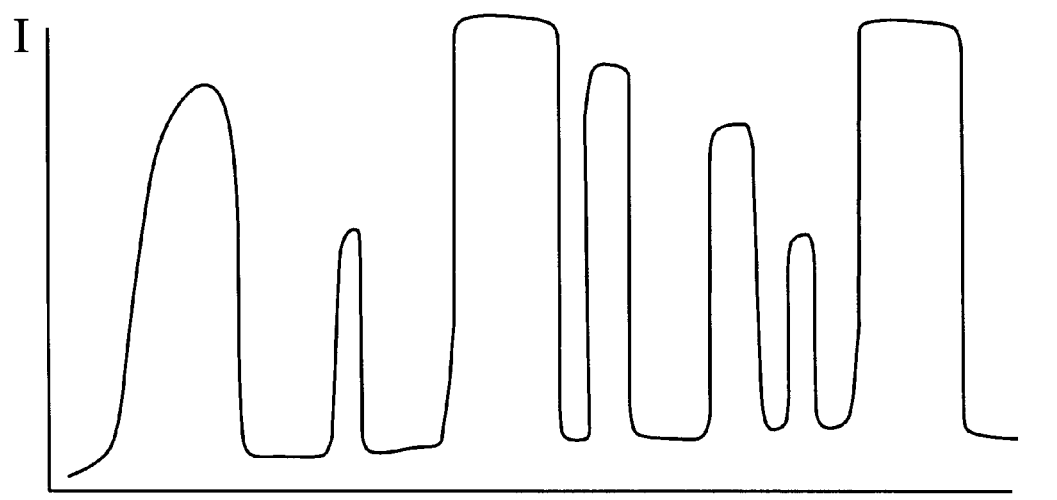

FIGS. 3A and 3B show graphs of radiation intensity over the calculation plane 210. Most conventional radiation treatments use a fairly steady radiation beam intensity, as shown in the graph of FIG. 3A. The radiation intensity over the affected area 212 of FIG. 2 may be approximately constant. However, in the field of intensity modulation, a superimposition of radiation fields may be used to maximize the radiation dose to a target, such as a tumor, and minimize the radiation dose to healthy tissue surrounding the target. The resulting graph of intensity over the area 212 is exemplified in FIG. 3B. The intensity of the radiation beam may vary dramatically throughout the affected area 212. Accordingly, an approximation of the fluence over one square of the calculation plane 210 would be entirely inaccurate for the remainder of the affected squares in the calculation plane 210.

Figure 4:
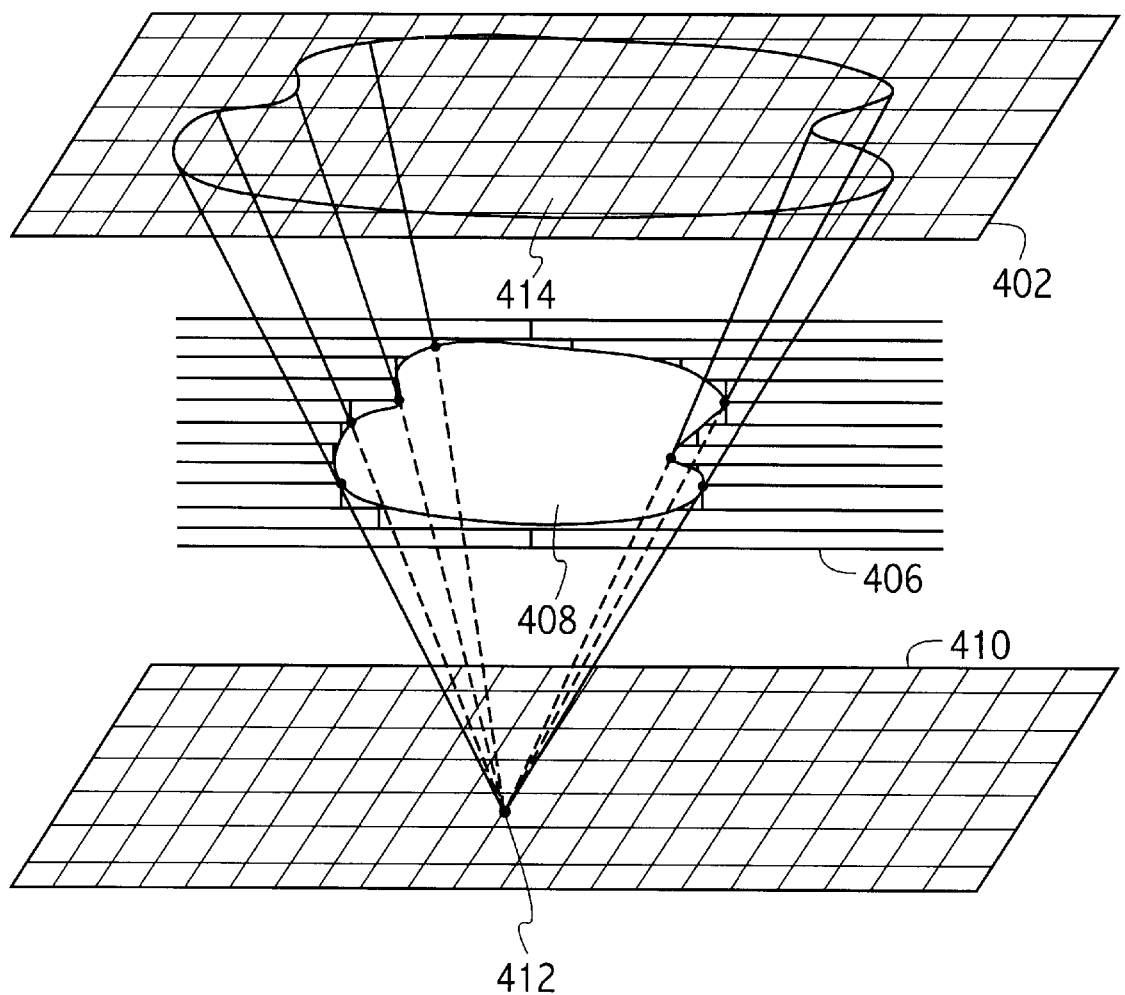
FIG. 4 is an illustration of an example of a method for calculating scatter radiation.

FIG. 4 illustrates an example of one method for calculating fluence over a calculation plane. FIG. 4 shows a collimator 406 positioned between a scattering plane 402 and a calculation plane 410. In this conventional method, a square on the calculation plane, herein referred to as a calculation point, may be analyzed by performing a ray tracing from the calculation point 412 to the collimator aperture 408. The aperture 408 may then be projected onto the scattering plane 402 such that projection 414 is defined on the scattering plane 402. This projection 414 should include all squares on the scattering plane 402 that may be a potential source of scattered radiation onto the calculation point 412.

In this method, the collimator 406 is treated as having an infinitesimal thickness. Assuming an infinitesimal thickness of a collimator 406 may cause inaccuracies in the scatter contribution of a calculation point. Additionally, this method may require a substantial amount of calculations.

It would be desirable to have a method for calculating scatter radiation contribution to a calculation point which is fast and accurate. The present invention addresses such a need.

Figure 5:
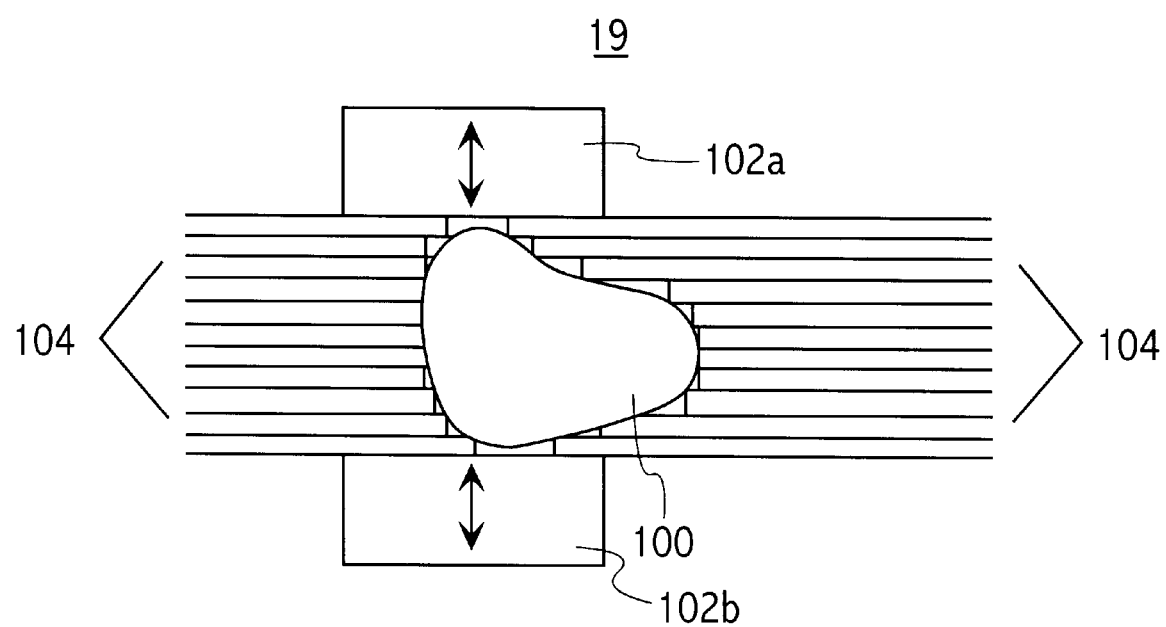
FIG. 5 is an illustration of a multi-leaf collimator suitable for use with an embodiment of the present invention.

FIG. 5 is an illustration of a multi-leaf collimator. In the example shown in FIG. 5, a multi-leaf collimator 19 is shown to be shaped around a target 100, such as a tumor. Tumor shapes are often irregular, and a multi-leaf collimator, such as the multi-leaf collimator manufactured by Siemens, facilitates the application of minimal radiation to non-tumor tissues by shaping itself close to the shape of the tumor.

Multi-leaf collimator 19 is shown to include leaves 104 located on either side of target 100. Additionally, multi-leaf collimator 19 may also include a set of jaws 102a–102b located perpendicular to leaves 104. Jaws 102a–102b may be movable in a direction perpendicular to the longitudinal axis of leaves 104. Accordingly, jaws 102a–102b may approach each other to reduce the size of the x-ray field, or move away from each other to increase the size of the x-ray field. Likewise, each leaf 104 may be moved along its longitudinal axis toward or away from an opposing leaf 104 to customize the x-ray field for a particular target 100, such as a tumor. The x-ray field is allowed to pass within the space between leaves 104 and jaws 102a–102b.

Figure 6A:
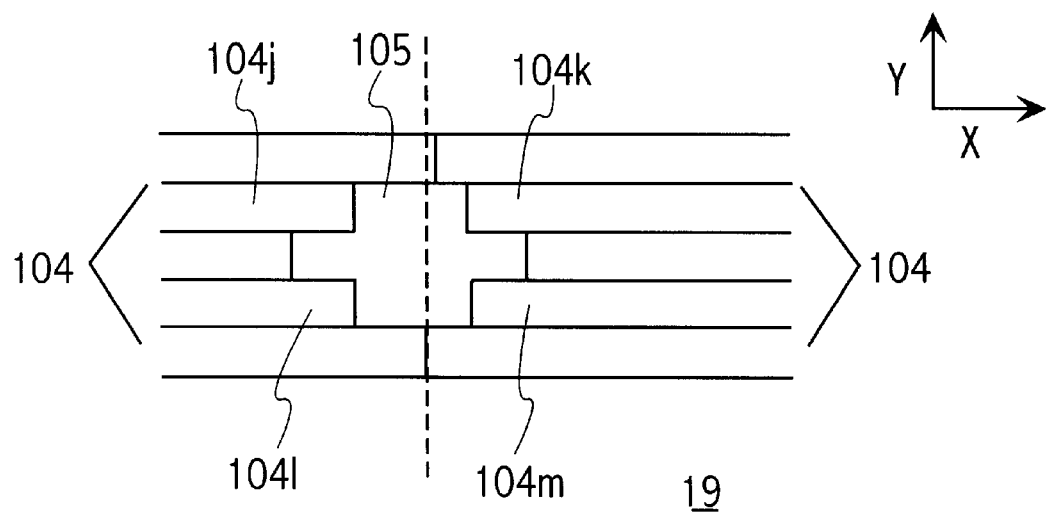
FIGS. 6A–6C show various perspectives of a collimator.
Figure 6B:
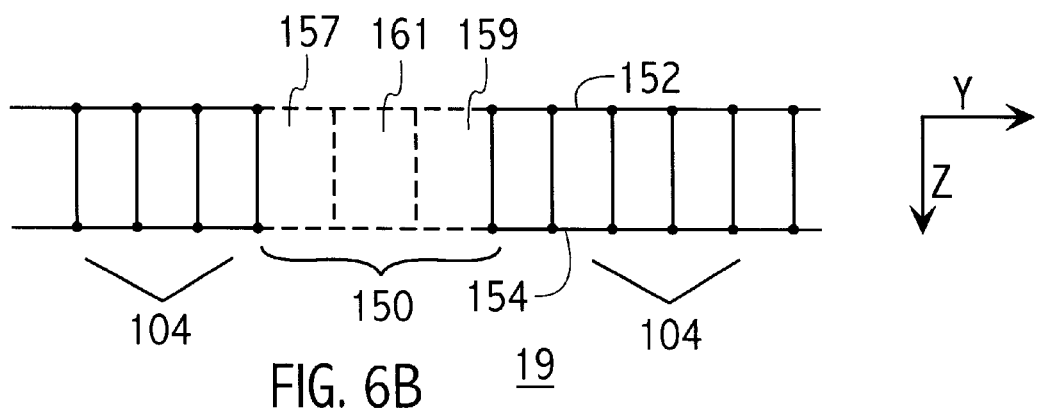
Figure 6C:
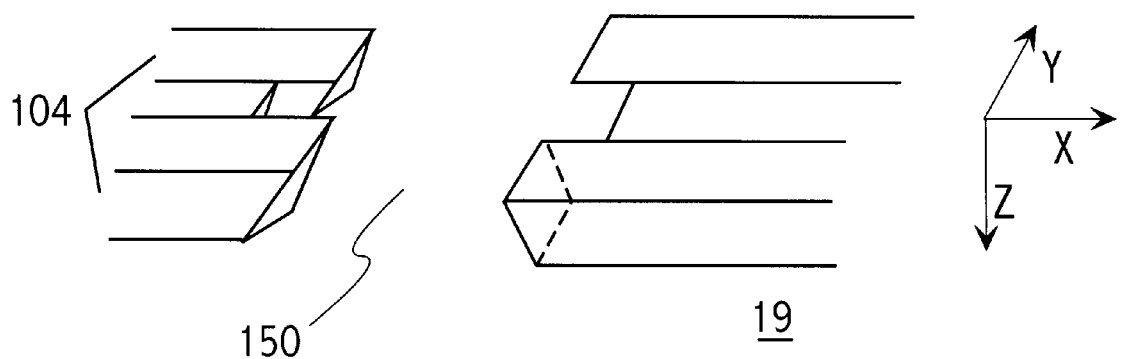

FIGS. 6A–6C show illustrations of collimator 19 from various perspectives. For simplicity, the illustrations and calculations related to the collimator 19 shown in the remaining figures exclude jaws 102a–102b of FIG. 5, however, in the calculations, the jaws may be considered as an extra pair of leaves in collimator 19. FIG. 6A shows collimator 19 as seen in the x-y plane. In this figure, an aperture 150 is shown to be created by leaves 104. FIG. 6B shows collimator 19 in the y-z plane, while FIG. 6C shows leaves 104 of collimator 19 in perspective, indicating its three dimensional (x, y, z) nature. To simplify the fluence calculation, the calculation is performed in a series of 2-dimensional calculations, according to an embodiment of the present invention, as will later be discussed in conjunction with the remaining figures.

Figure 7:
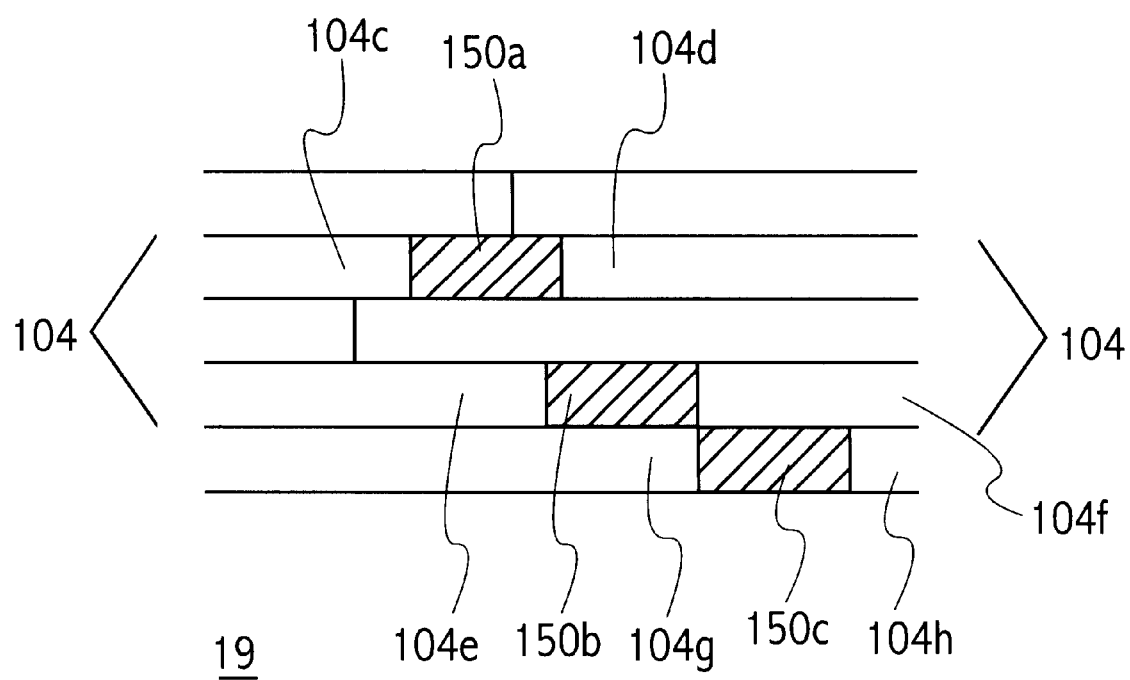
FIG. 7 illustrates multiple polygons which may be created by a collimator.

FIG. 7 is an illustration of collimator 19 with multiple apertures or polygons 150A–150C created by leaves 104. Each polygon 150A–150C may be analyzed for scatter contributions, as will later be discussed in conjunction with the remaining figures.

Figure 8:
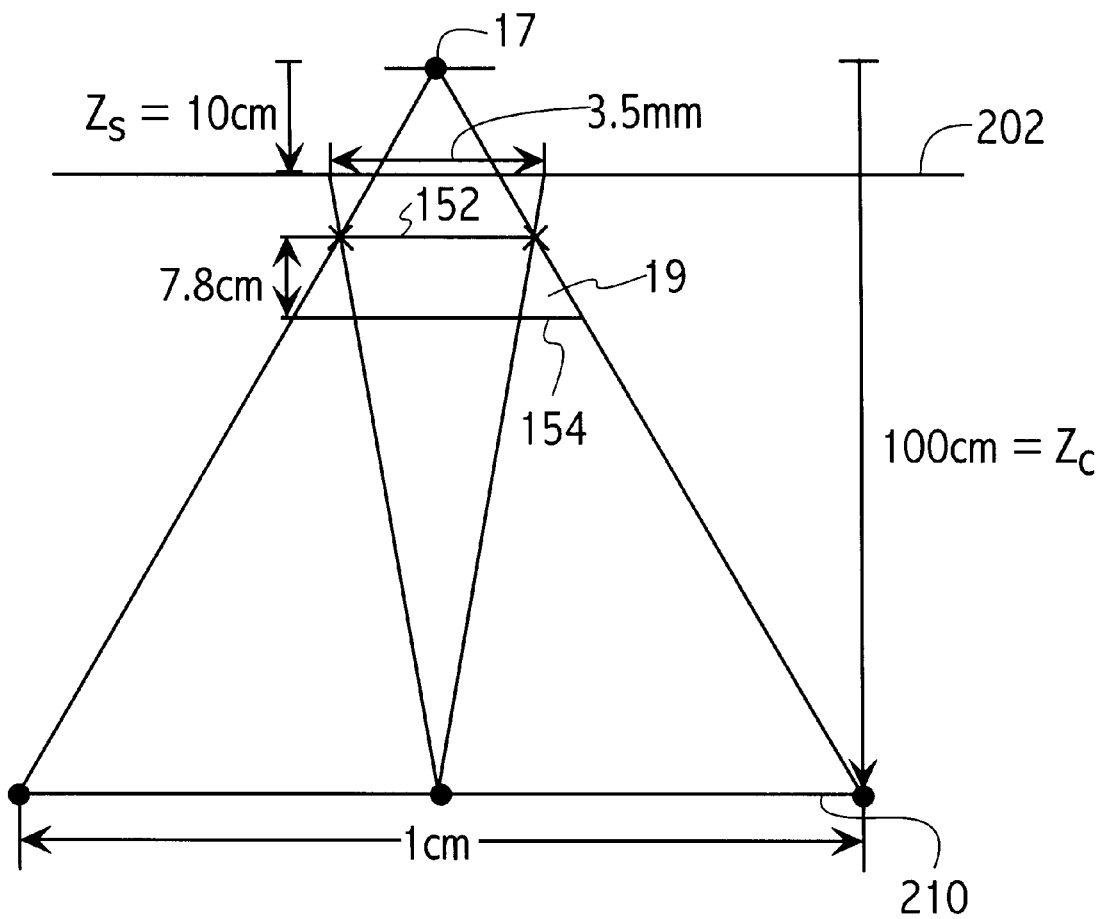
FIG. 8 is an illustration of scattering plane and calculation plane geometries according to an embodiment of the present invention.

FIG. 8 shows an illustration of an example of comparative proportions for the scattering plane and the calculation plane. In this example, scattering plane 202 is approximately 10 cm from the source of the radiation beam, directly below flattening filter 200, and calculation plane 210 is located approximately 100 cm from the source of the radiation beam, target 17. The radiation beam flows through scattering plane 202 and collimator 19 and is projected onto calculation field 210. An example of the thickness of collimator 19 is 7.8 cm. In this example, the projection of the leaf width formed by the radiation beam as it travels from target 17 through collimator 19 and onto calculation plane 210 is approximately 1 cm. Note that the Figures are not to scale. A projection of the collimator leaf top width from the calculation point onto the scattering plane 202 may be approximately 3.5 mm. Squares located on the scattering plane 202 may be approximately 1 mm×1 mm, while the rectangles in the calculation plane may be approximately 1 cm by an arbitrary amount, such as 1 cm. An example of the number of squares on calculation plane 210 is approximately 100 and the number of squares in scattering plane 202 could be as many as 10,000 squares.

The selection of a square in the scattering plane 202 should be such that the width of the scattering square should be smaller than a scattering strip according to an embodiment of the present invention. The scattering squares should also be smaller than a square which was projected onto scattering plane 202 through collimator 19 from a point on calculating plane 210. Accordingly, an example of a size of a scattering square is 1 mm×1 mm.

Further details of scattering strips will later be discussed in conjunction with the remaining figures.

Figure 9:
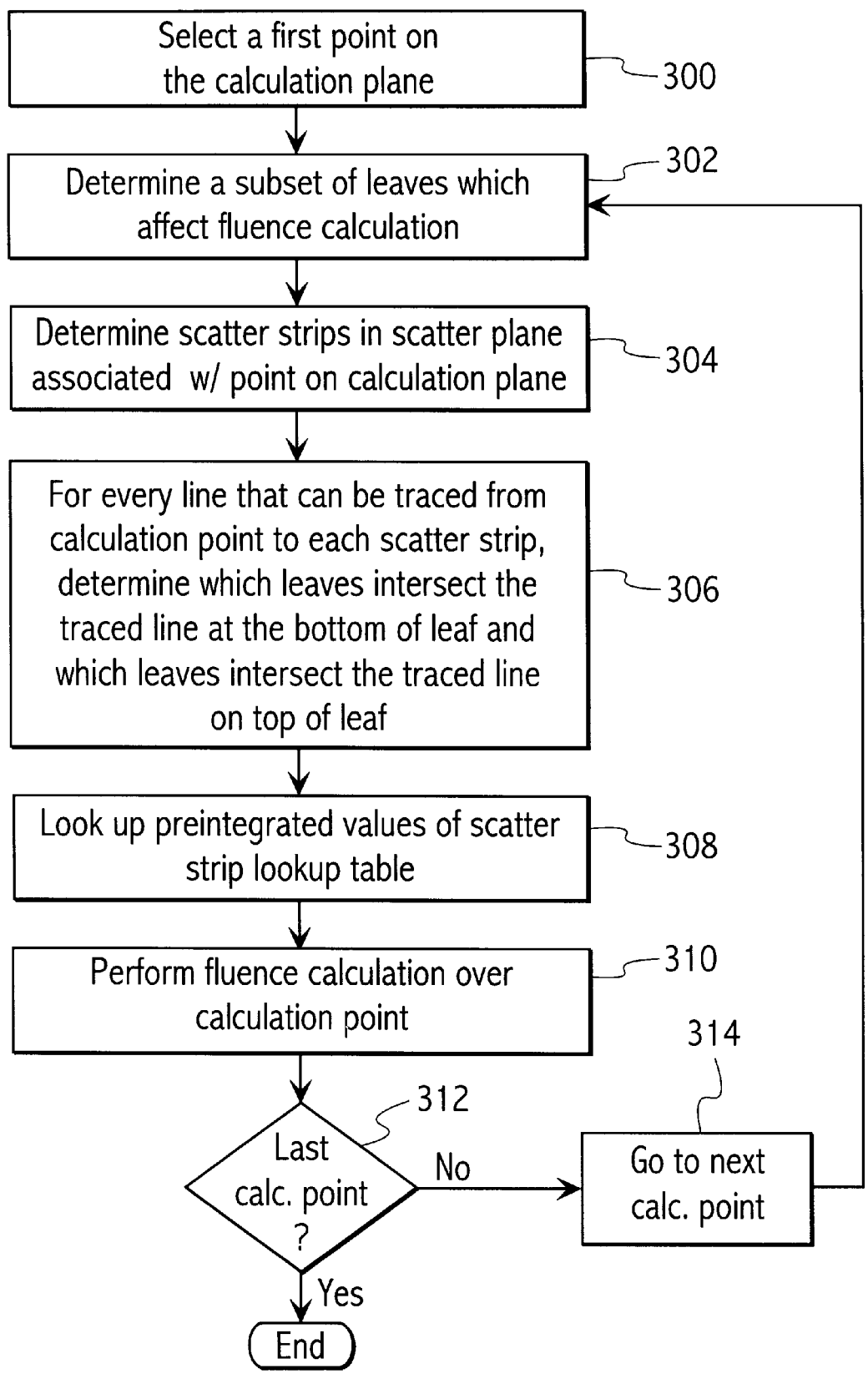
FIG. 9 is a flow diagram of a method according to an embodiment of the present invention for calculating scatter radiation.

FIG. 9 is a flow diagram of a method according to an embodiment of the present invention for calculating scatter radiation. Initially, a first point on the calculation plane is selected (step 300). As previously mentioned, a point on the calculation plane refers to a segment of the calculation plane, such as a calculation square. Further details of the selection of a first point on the calculation plane will later be discussed in conjunction with FIG. 10A.

A subset of collimator leaves which may affect the fluence calculation is determined (step 302). Details of determining such a subset of collimator leaves is later discussed in conjunction with FIG. 10A–13, 16–17b. Scatter strips in the scattering plane which are associated with the selected point on the calculation plane is then determined (step 304). A scatter strip may include a portion of a scatter square, a single scatter square, multiple scatter squares, or any combination thereof, of the scattering plane. For every line that can be traced from the selected calculation point to each scatter strip on the scattering plane, the leaves which intersect the traced line on the bottom of the leaf and the leaves which intersect the traced line on the top of the leaf are determined (step 306). Further details of this determination will later be discussed in conjunction with FIGS. 10A–13, 15, 17A–17B. Pre-integrated values of the scatter strip are then looked up in a lookup table (step 308). Details of the pre-integrated values of the scatter strips will also later be discussed in conjunction with FIGS. 10A–10C, and 18–20.

The fluence calculation is then performed over the calculation point (step 310). It is then determined whether this calculation point is the last calculation point (step 312). If it is the last calculation point, then the fluence calculation is complete, assuming that there is only one polygon to calculate over the collimator. If, however, this is not the last calculation point, then the next calculation point is analyzed (step 314), and a subset of leaves which affect the fluence calculation for this next calculation point is then determined (step 302).

FIG. 10A–19C are further flow diagrams of a method according to an embodiment of the present invention for calculating fluence of the scatter contribution over the calculation plane. Initially, the number of polygons to be analyzed is determined (step 400). An example of polygons to be determined is shown in FIG. 7. In the example shown in FIG. 7, the collimator 19 is shown to be arranged to create polygons 150A–150C. Further details of the determination of the number of polygons to be analyzed will later be discussed in conjunction with FIG. 14.

One of the polygons is then selected (step 402). A y-value of a calculation point in the calculation plane is then selected (step 404). At this step, the y-z plane is referenced, accordingly, it is not yet necessary to know the x values. The analysis for this one y value may be applied to all calculation points that have this same y value, even if they have different x values. At this step, one may conceptualize a calculation line rather than a calculation point, with the line having the same y and z coordinates and the line extending over all values of x (perpendicular to the y-z plane).

A maximum collimator leaf and a minimum collimator leaf for the selected polygon is then determined (step 406). FIG. 6b shows an example of a maximum leaf 159 and a minimum leaf 157 in collimator 19. In this example, the maximum and minimum refers to the first and last leaves of the polygon, respectively. These maximum and minimum leaves 159 and 157 bracket the range of scatter strips that will be visible to a calculation point. The dashed lines represent all the leaves between and including the maximum and the minimum leaf. In determining the maximum and minimum leaves, all the leaves that are open in the polygon should be considered, not just those visible in a y-z perspective.

A range of leaves between the minimum and maximum leaves of the polygon is then determined (step 408). In the example shown in FIG. 6B, the range of leaves between the minimum and maximum leaves includes leaf 161.

Figure 13:
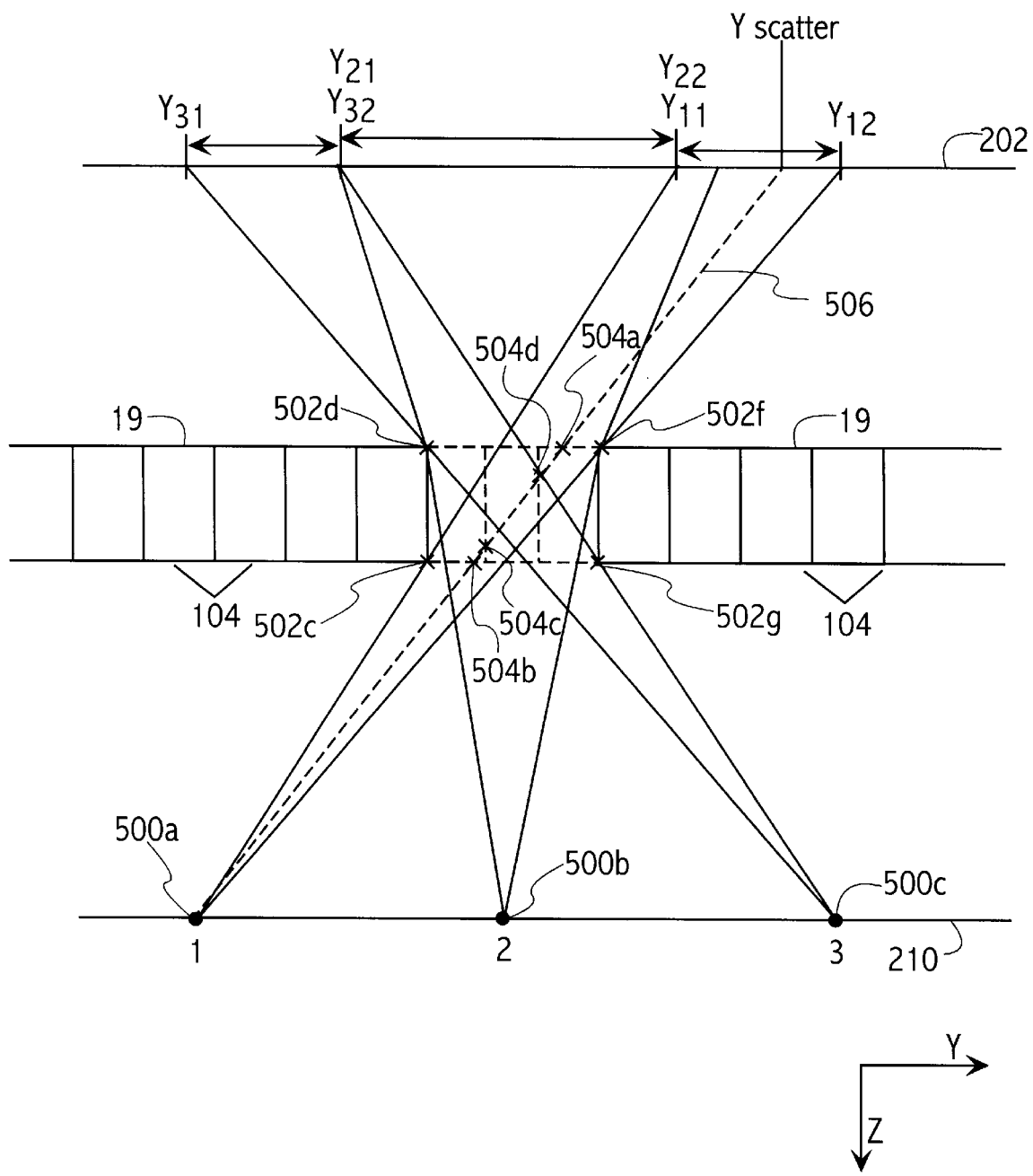

Collimator leaf points to be intersected by line traces from the selected calculation point to the scattering plane are established (step 410). At this point, all the calculations are performed for the y-z plane only. A line is traced from the line $y=y_c$, $z=100$ to the line $y=y_s$, $z=10$, assuming the values shown in the example of FIG. 8. Consider a perpendicular line from the line in the calculation plane that has one y value but several x values associated with it to the line in the scattering plane that has one y value but several x values associated with it also. In the y-z plane view, the x dimension has been collapsed into a single value, so that all x values are treated the same way in this plane. An example of collimator leaf points to be intersected by line traces from the calculation point to the scattering plane are shown in FIG. 13 (504a–d).

A minimum y and a maximum y of the scattering plane is then determined (step 412). The minimum and maximum y-values are the y-values of a projection from the calculation point to the scattering plane. For example, FIG. 13 is yet another diagram showing the collimator 19 located between calculation plane 210 and scattering plane 202.

This perspective is shown in the y-z plane. As shown in this example, each calculation point 500A–500C on the calculation plane 210 is shown to have a projection onto the scattering plane 202. Each projection has a minimum y and a maximum y of the scattering plane 202. In this example, the minimum y associated with calculation point 500A is $y_{11}$, while the maximum y is $y_{12}$. Likewise, the minimum y and maximum y-values associated with calculation point 500B is $y_{21}$, and $y_{22}$; and the minimum and maximum y-value associated with calculation point 500C is $y_{31}$ and $y_{32}$.

For every line that can be traced from the calculation point on the calculation plane to each scatter strip within $y_1$ and $y_2$ ($y_s$), a point at leaf bottom level and a point at leaf top level are determined which intersects the traced line (step 414). The example shown in FIG. 13 shows a traced line 506 which is traced from the calculation point 500A to a scatter strip at $y_s$ of the scattering plane 202. The traced line 506 intersects a leaf bottom 504B and a leaf top level 504A.

Figure 10A:
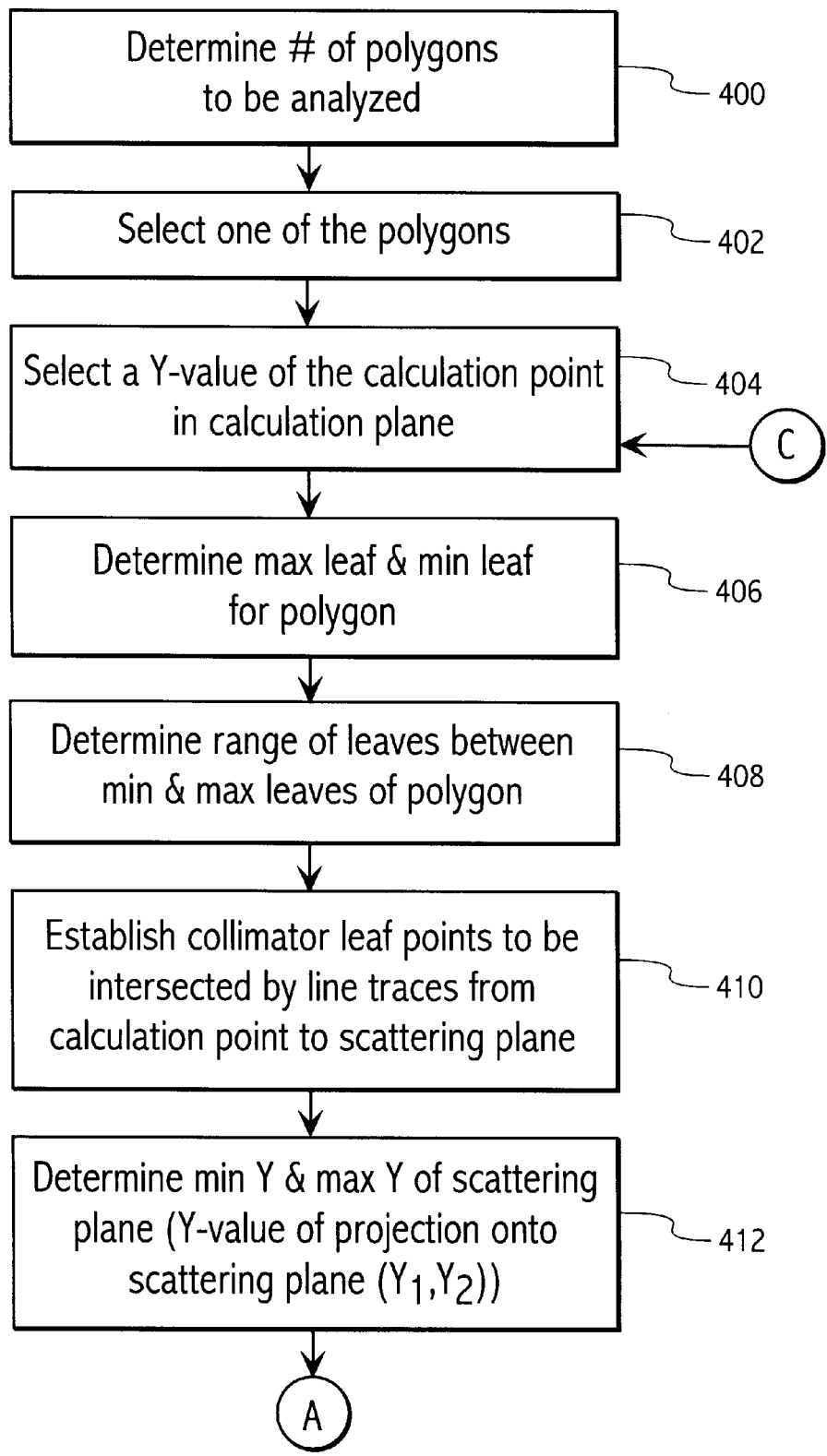
FIGS. 10A–10C are additional flow diagrams of a method according to an embodiment of the present invention for calculating scatter radiation.
Figure 10B:
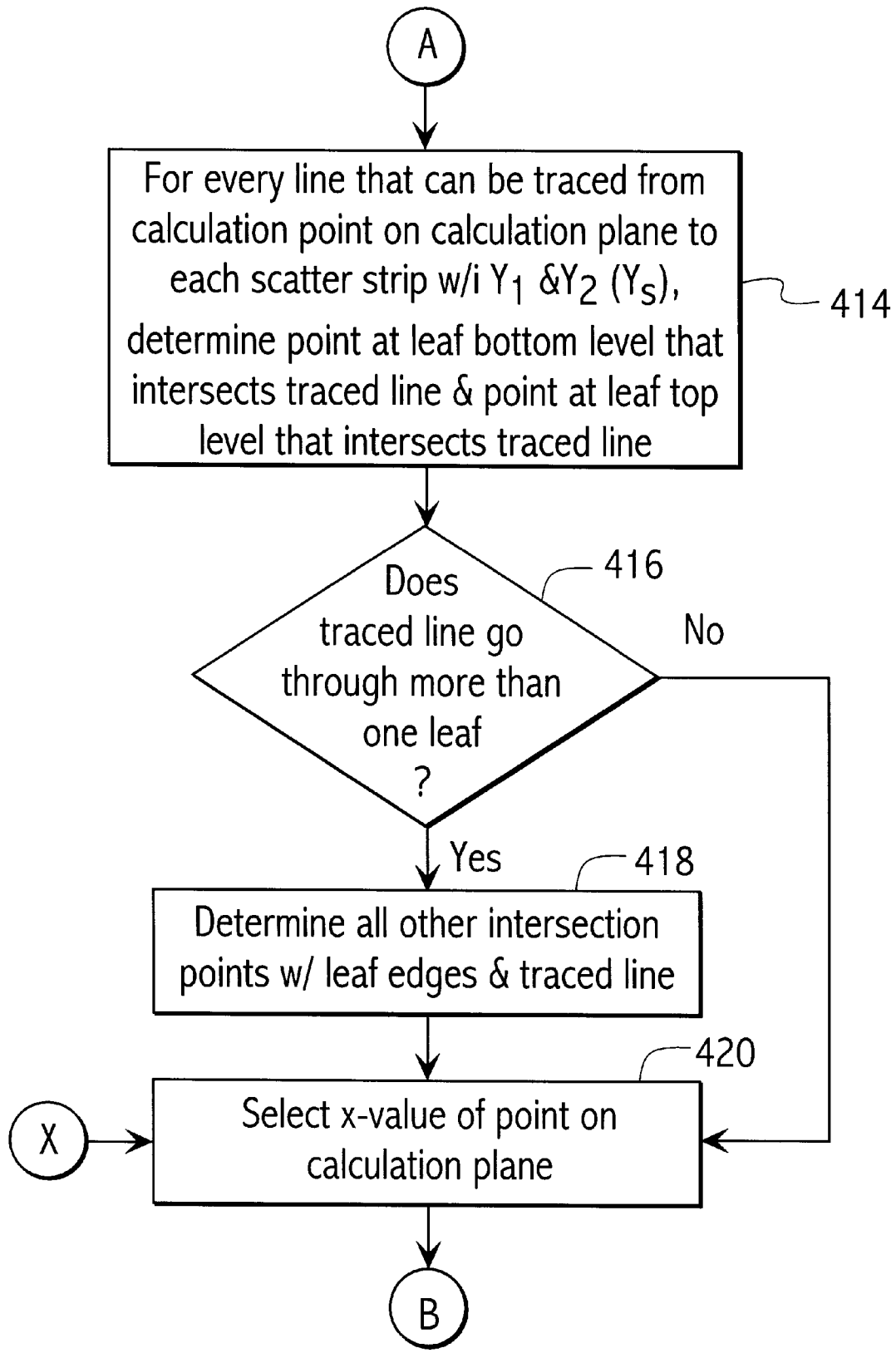

It is then determined whether the traced line traverses through more than one leaf (step 416 of FIG. 10B). Note that an intersection between a line and a leaf indicates a two-dimensional intersection, not a three-dimensional intersection. In three-dimensions, a ray does not necessarily intersect a given leaf, however, in a two dimensional collapsed view, such as the y-z plane view shown in FIG. 13, the ray appears to intersect the leaf.

In the example shown in FIG. 13, the traced line 506 does traverse through more than one leaf. When the trace line moves through more than one leaf, all of other intersection points with the leaf edges and the traced line are determined (step 418). In the example shown in FIG. 13, intersection points 504C and 504D are determined. Thereafter, an x-value of the point on the calculation plane is selected (step 420). If the traced line does not go through more than one leaf (step 416), then an x-value of calculation point on the calculation plane is selected (step 420).

Figure 10C:
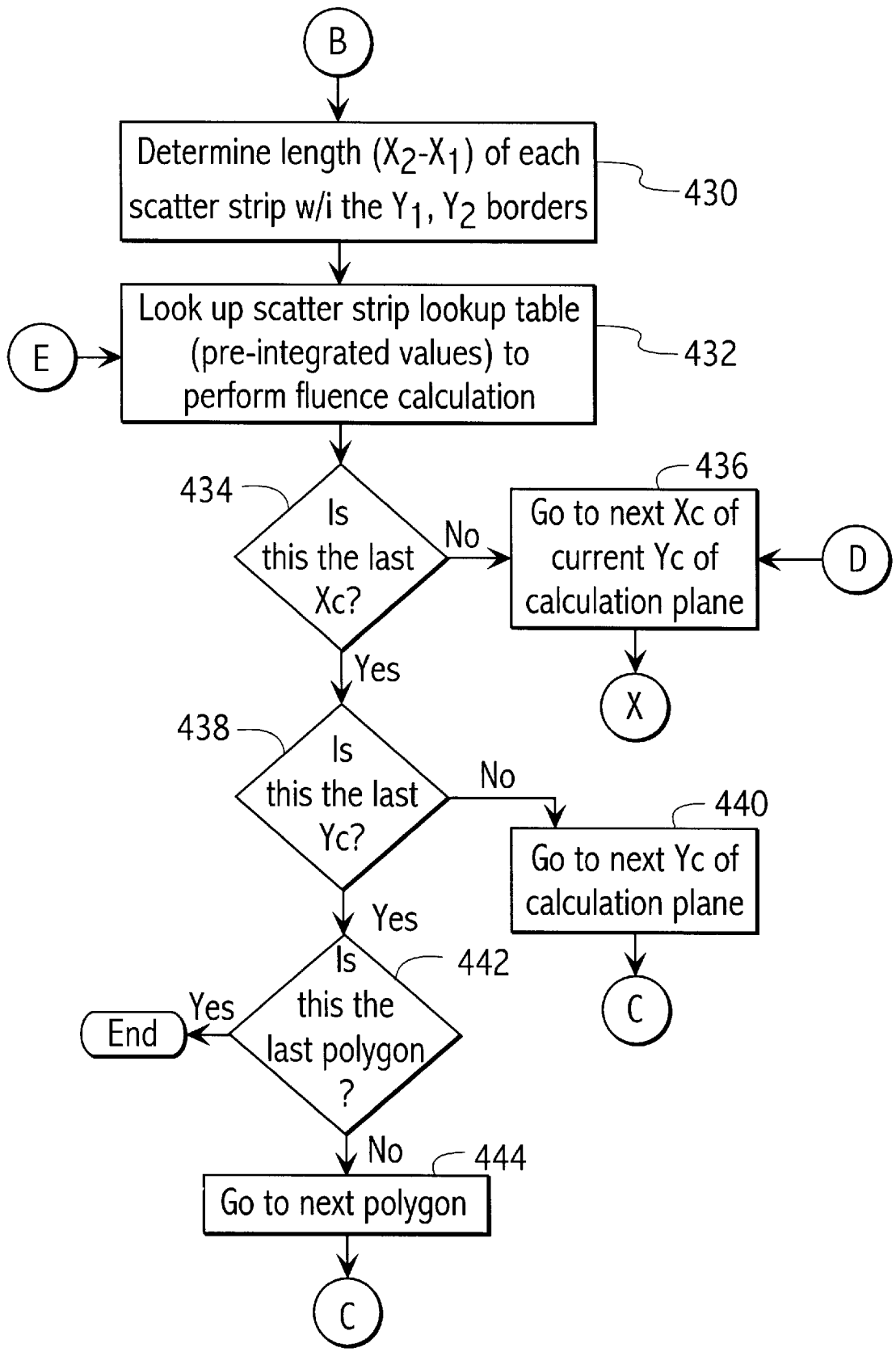

The length ($x_2-x_1$) of each scatter strip ($y_s$) within the $y_1$, $y_2$ borders is determined (step 430 of FIG. 10C). In the example shown in FIG. 13, the perspective is shown in the y-z plane. Accordingly, only $y_s$ can be seen on the scattering plane 202. In this example, all scattering strips are perpendicular to the y-z plane, so only the intersection of each of these strips with the y-z plane are visible. However, in the perspective shown in FIG. 11, a similar diagram is shown in the x-y plane. In the x-y plane, the scattering plane 202 shows that a scattering strip 520 is shown to be located on the scattering plane 202. The scattering strip 520 has a length of $x_2-x_1$ at $y_s$. The scattering strip 520 is the scattering strip associated with the calculation point 500b.

A scatter strip lookup table may be referenced to perform a fluence calculation of the calculation point (step 432). According to an embodiment of the present invention, the scattering strip lookup table includes pre-integrated values that correspond to each scatter strip. Further details of the scatter strip lookup table and the fluence calculation will later be discussed in conjunction with FIGS. 18–20.

It is then determined whether the x-value of the calculation point ($x_c$) is the last $x_c$ (step 434). If this is not the last $x_c$, then the next $x_c$ of the current y of the calculation plane ($y_c$) is analyzed (step 436 of FIG. 10C). Thereafter, a new x value of a point on the calculation plane is selected (420 of FIG. 10B).

If the current $x_c$ is not the last $x_c$, then it is determined whether the current y of the calculation plane ($y_c$) is the last $y_c$ (step 438). If the current $y_c$ is not the last $y_c$, then the next $y_c$ of the calculation plane is analyzed (step 440). Accordingly, a y-value of the new calculation point in the calculation plane is then selected (step 404 of FIG. 10A).

If this $y_c$ is the last $y_c$, then it is determined whether this polygon is the last polygon shaped by the collimator (step 442). If this is the last polygon, then the fluence calculation is complete. If, however, this is not the last polygon, then the next polygon is analyzed (step 444). Accordingly, a new y-value of the new calculation point in the calculation plane is selected to analyze the new polygon (step 404 of FIG. 10A).

Figure 14:
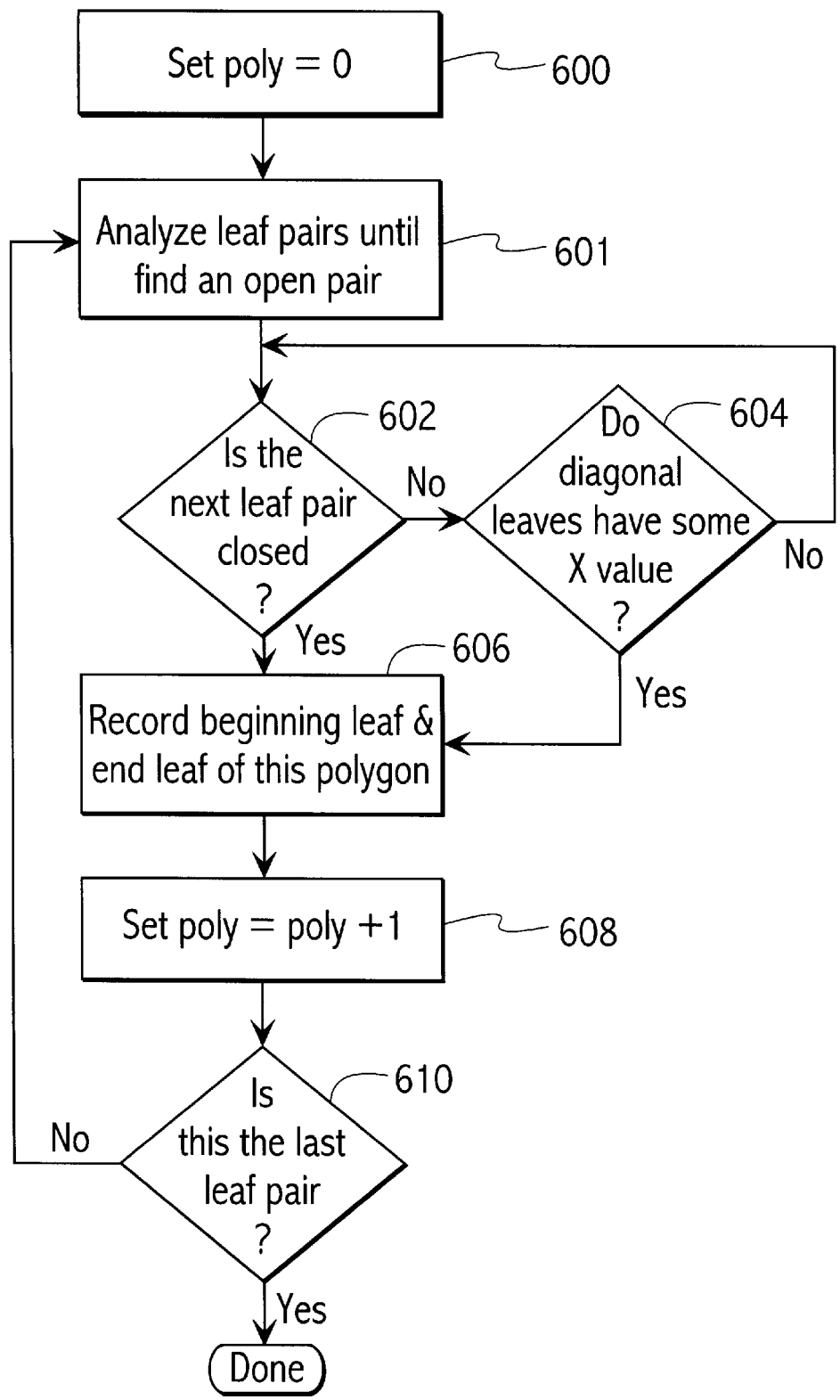
FIG. 14 is a flow diagram of a method according to an embodiment of the present invention for determining the number of polygons in a collimator.

FIG. 14 is a flow diagram of a method according to an embodiment of the present invention for determining the number of polygons, such as the determination of step 400 of FIG. 10A. A variable, "poly", is initially set to 0 (step 600), and all collimator leaf pairs are analyzed until a first open pair of collimator leaves are found (step 601). It is then determined whether the next leaf pair analyzed after the first open pair is closed (step 602). If the next leaf pair is not closed, then it is determined whether diagonal leaves have the same x-value (step 604). For example, in FIG. 7, the leaf pair 104C and 104D is open, while the next leaf pair is closed. Also, the leaf pair including leaves 104E and 104F is open and diagonal leaves 104F and 104G have the same x-value since their adjacent corners are aligned.

If the diagonal leaves do not have the same x-value (step 604), then the next leaf pair is analyzed to determined if it is closed (step 602). If, however, diagonal leaves do have the same x-value (step 604), or the next leaf pair is closed (step 602), then the beginning leaf pair and the end leaf pair of this polygon are recorded (step 606). In the example shown in FIG. 6A, the beginning leaf pair 104J and 104K would be recorded, and the end leaf pair 104L and 104M of polygon 150 would be recorded. In this example, the beginning leaf pair 104J and 104K is the first pair that is open, and the end leaf pair 104L and 104M is the last pair that is open.

Thereafter, the next polygon is analyzed ("poly" is set=to "poly"+1) (step 608). It is then determined whether this leaf pair is the last leaf pair (step 610). If this leaf pair is not the last leaf pair, then the process starts over in step 601 to find the very next open pair. If, however, this leaf pair is the last leaf pair, then the number of polygons has been determined.

Figure 15:
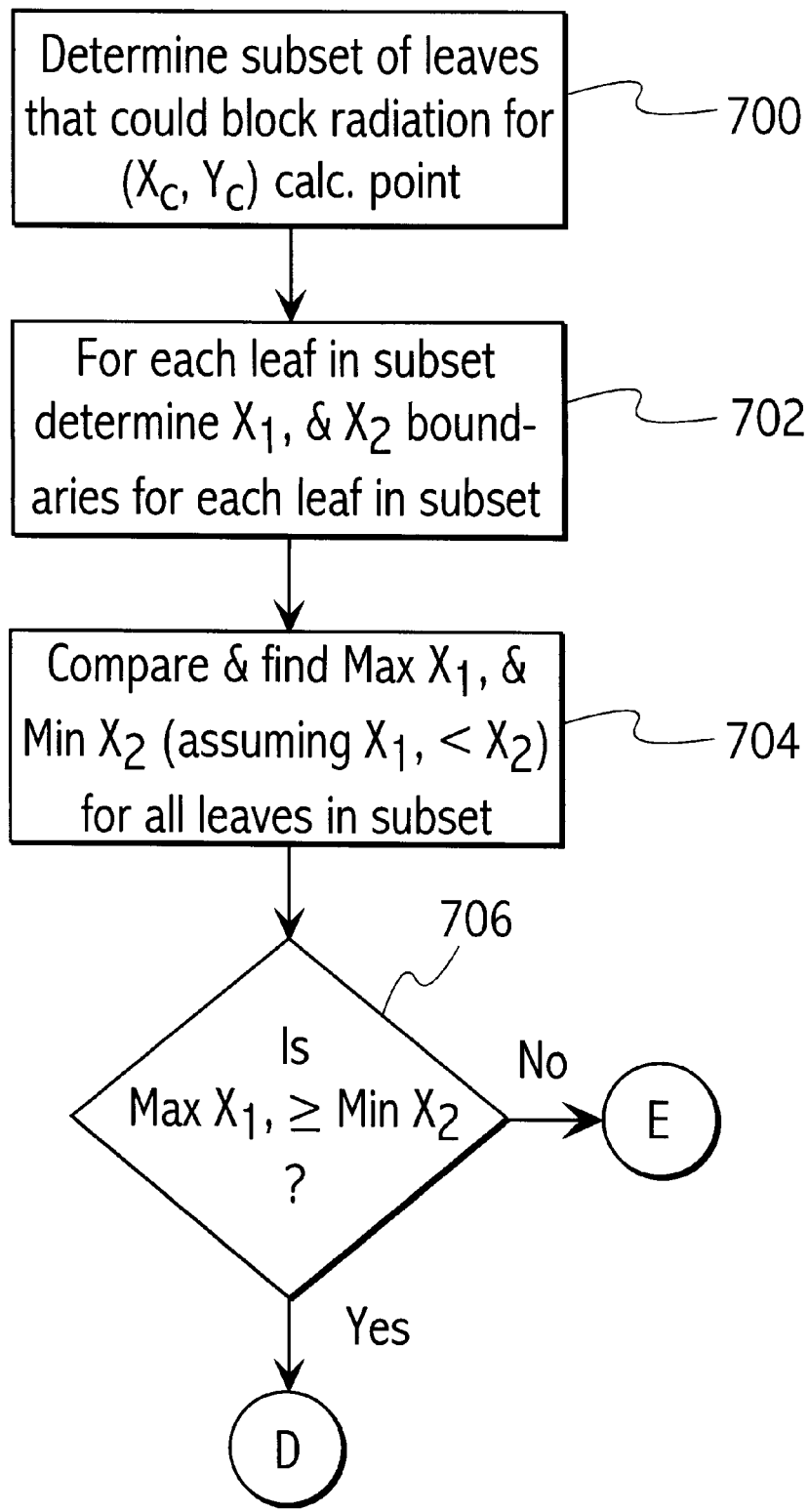
FIG. 15 is a flow diagram of a method according to an embodiment of the present invention for determining a length of each scatter strip.

FIG. 15 is a flow diagram of a method according to an embodiment of the present invention for determining a length $(x_2-x_1)$ of each scatter strip, such as the determination made in step 430 of FIG. 10C. With regard to the hypothetical construct of the scattering plane, the scatter strip may include a portion of a scatter square, a single scatter square, multiple scatter squares, or any combination thereof.

A subset of collimator leaves that could block radiation for an analyzed calculation point $(x_c, y_c)$ is determined (step 700). Further details of determining the subset of leaves is later discussed in conjunction with FIG. 16. For each leaf in the subset, an $x_1$ and $x_2$ boundary for each collimator leaf in the subset is determined (step 702). $X_1$ is a projection of a ray from the calculation point on the calculation plane to the scattering plane traversing across a leaf on side A of the collimator (see FIG. 11), while $x_2$ is a projection of a ray from the calculation point to the scattering plane traversing across a leaf on side B of the collimator. Details of such determination is later discussed in conjunction with FIGS. 17A and 17B. All of the $x_1$ and $x_2$ for all of the collimator leaves in the subset are compared and a maximum $x_1$ and a minimum $x_2$ (assuming $x_1$ is less than $x_2$) is found for all leaves in the subset (step 704). Details of finding the maximum $x_1$ and the minimum $x_2$ is later discussed in conjunction with FIGS. 17A and 17B.

It is then determined whether the maximum $x_1$ is greater or equal to the minimum $x_2$ (step 706). The $x_1$ and $x_2$ of each leaf in the subset is an indication of how far each leaf is out into the radiation field. The maximum $x_1$ and the minimum $x_2$ are usually, but not always, associated with the leaves which are the furthest out into the radiation field from each side of the collimator leaves. For example, in the diagram shown in FIG. 11, leaves 104A and 104B are the leaves associated with the maximum $x_1$ and the minimum $x_2$, respectively, for calculation point 500b, and they also happen to be the furthest leaves out into the radiation field for sides A and B of the collimator leaves.

The maximum $x_1$ and the minimum $x_2$ are actually associated with the leaves that block out the most radiation, and this is not necessarily the leaves that are furthest out into the field. While that is the case for a calculation point that is not behind any leaf bank (that is $x_c$>XAMAX and $x_c$<XBMIN, as is the case with point 500b of FIG. 11), for points such as 500a and 500c that are behind leaf banks, the maximum $x_1$ and the minimum $x_2$ may be associated with leaves other than the furthest out in the radiation field. For example, if leaf 104c in FIG. 11 had its edge 580 just slightly to the left of edge 582 of leaf 104a, then edge 580 would intersect the ray trace going from 500a to point 572, rather than edge 582. In that situation, leaf 104c would block more radiation despite it not being the furthest out in the radiation field.

If maximum $x_1$ is greater or equal to the minimum $x_2$, then no radiation will be received at that calculation point. Accordingly the next point on the calculation plane is analyzed via step 436 of FIG. 10C. If, however, maximum $x_1$ is less than minimum $x_2$, then the scatter strip lookup table is referenced to perform the fluence calculation (step 432 of FIG. 10C).

Figure 16:
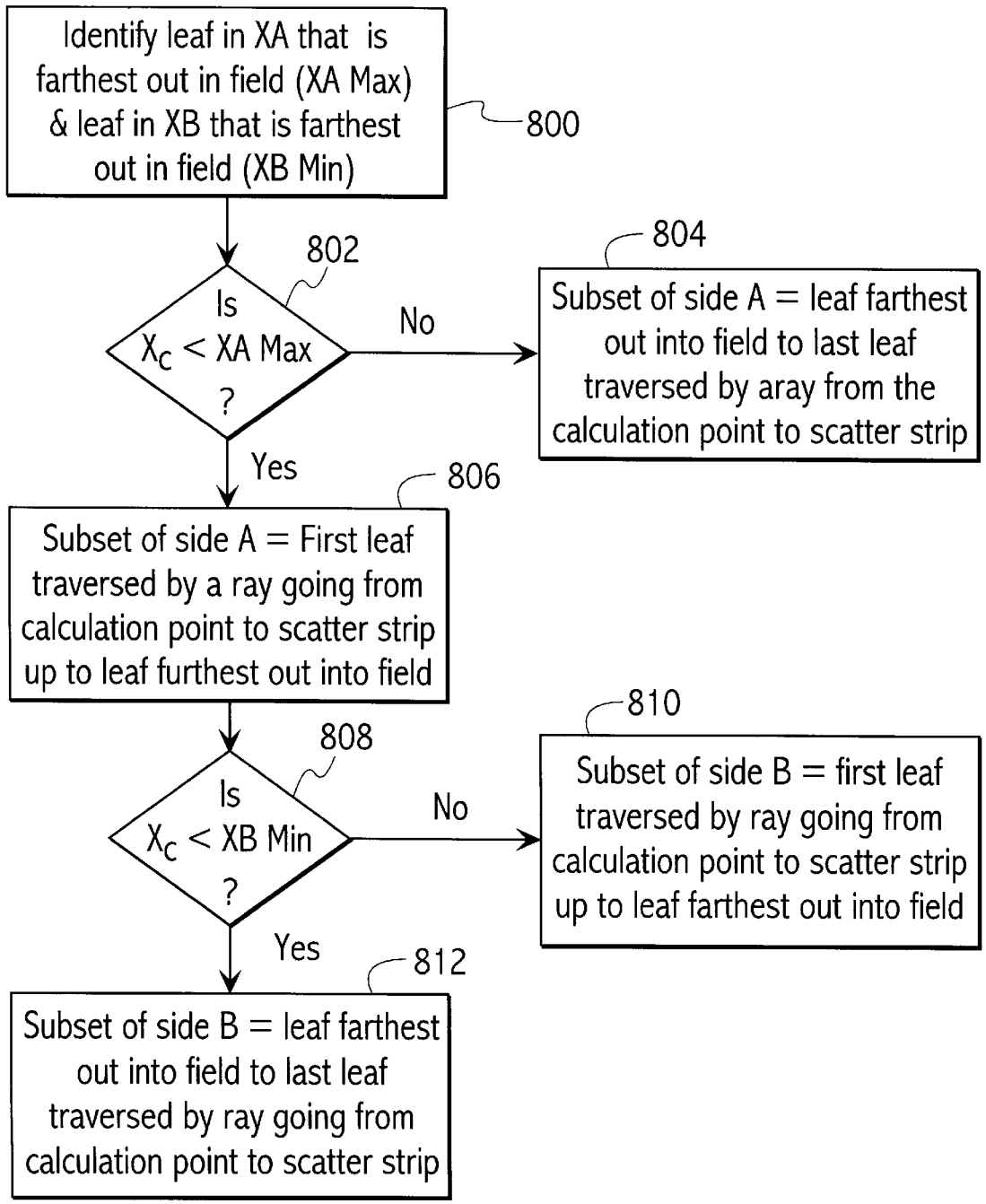
FIG. 16 is a flow diagram of a method according to an embodiment of the present invention for determining a subset of collimator leaves.

FIG. 16 is a flow diagram of the method according to an embodiment of the present invention for determining a subset of leaves that could block radiation for a particular calculation point $(x_5, y_c)$, such as the determination made in step 700 of FIG. 15. Initially, a leaf that is the furthest out in the radiation field on either side of the collimator is identified (step 800). In the example shown in FIG. 11, the collimator 19 has leaves on s side "A" and on side "B". In the example shown in FIG. 11, the leaf furthest out in the radiation field on the "A" side is shown to be leaf 104A. The leaf which is furthest out into the field on the "B" side is shown to be leaf 104B. These leaves have been designated as XAMAX and XBMIN, respectively.

It is then determined whether $x_c$ of the current calculation point is less than XAMAX (step 802). In the example shown in FIG. 11, calculation point 500A is located in a position such that the $x_c$ of the calculation point 500A is less than the x associated with leaf 104A which is the furthest out into the radiation field on side "A" (XAMAX). Calculation points 500B and 500C are shown to have an $x_c$ which is greater than or equal to XAMAX. Note that XAMAX is an x value associated with the position of the leaf furthest out into the radiation field on side A of the collimator, such as leaf 104a of FIG. 11, wherein the x value is a projection down to the calculation plane from the target. FIG. 8 shows an example of a projection down to the calculation plane 210 from the target 17.

If $x_c$ is not less than XAMAX, than the subset of leaves of side "A" is the set of leaves from the leaf furthest out into the field to the last leaf traversed by a ray from the calculation point to the scatter strip (step 804). In the example shown in FIG. 11, the subset is subset 560. If, however, $x_c$ is less than XAMAX, then the subset of leaves of side "A" is defined by the first leaf traversed by a ray going from the calculation point to the scatter strip up to the leaf that is the furthest out into the field (step 806). In the example shown in FIG. 11, this subset would be subset 562.

It is then determined whether $x_c$ is less than XBMIN (step 808). The XBMIN value is also an x value projected onto the calculation plane from the target. The XBMIN value is associated with the position of the leaf furthest out into the radiation field on side B of the collimator, such as leaf 104b of FIG. 11. In the example shown in FIG. 11, calculation points 500A and 500B are shown to have an $x_c$ less than XBMIN, while calculation point 500C is shown to have an $x_c$ greater or equal to XBMIN. If the $x_c$ of the calculation point is greater or equal to XBMIN, then the subset of leaves for side "B" is defined by the first leaf traversed by a ray going from the calculation point to the scatter strip up to the leaf furthest out into the field (step 810). In the example shown in FIG. 11, this subset only includes leaf 104B.

If the $x_c$ of the calculation point is less than XBMIN, then the subset of leaves of side "B" is defined by the leaf furthest out into the field to the last leaf traversed by a ray going from the calculation point to the scatter strip (step 812). In the example shown in FIG. 11, this subset includes all of the leaves shown inside "B".

Figure 17A:
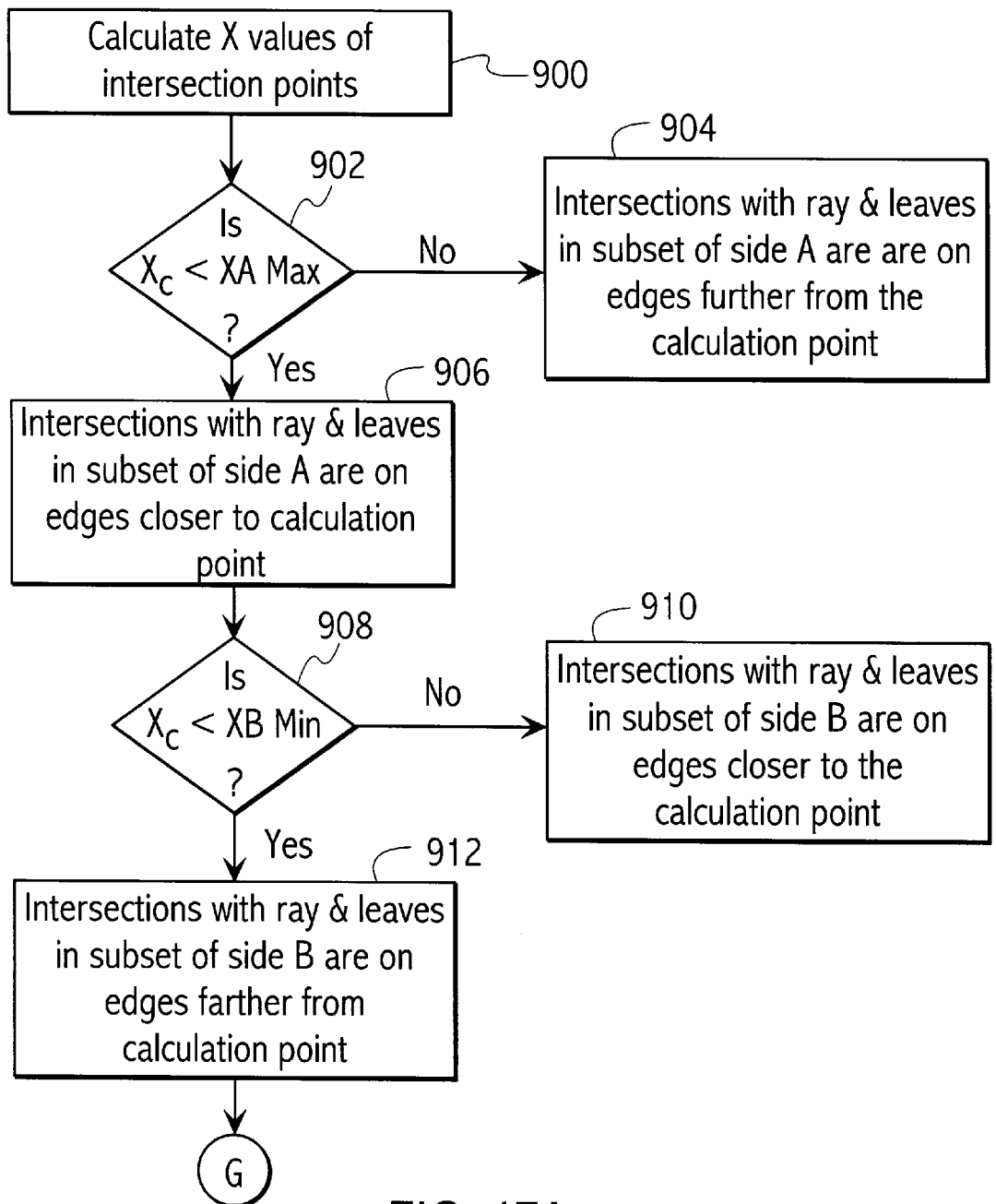
FIGS. 17A–17B are flow diagrams of a method according to an embodiment of the present invention for determining minimum and maximum boundaries for all scatter strips of all leaves in the subset of leaves.
Figure 17B:
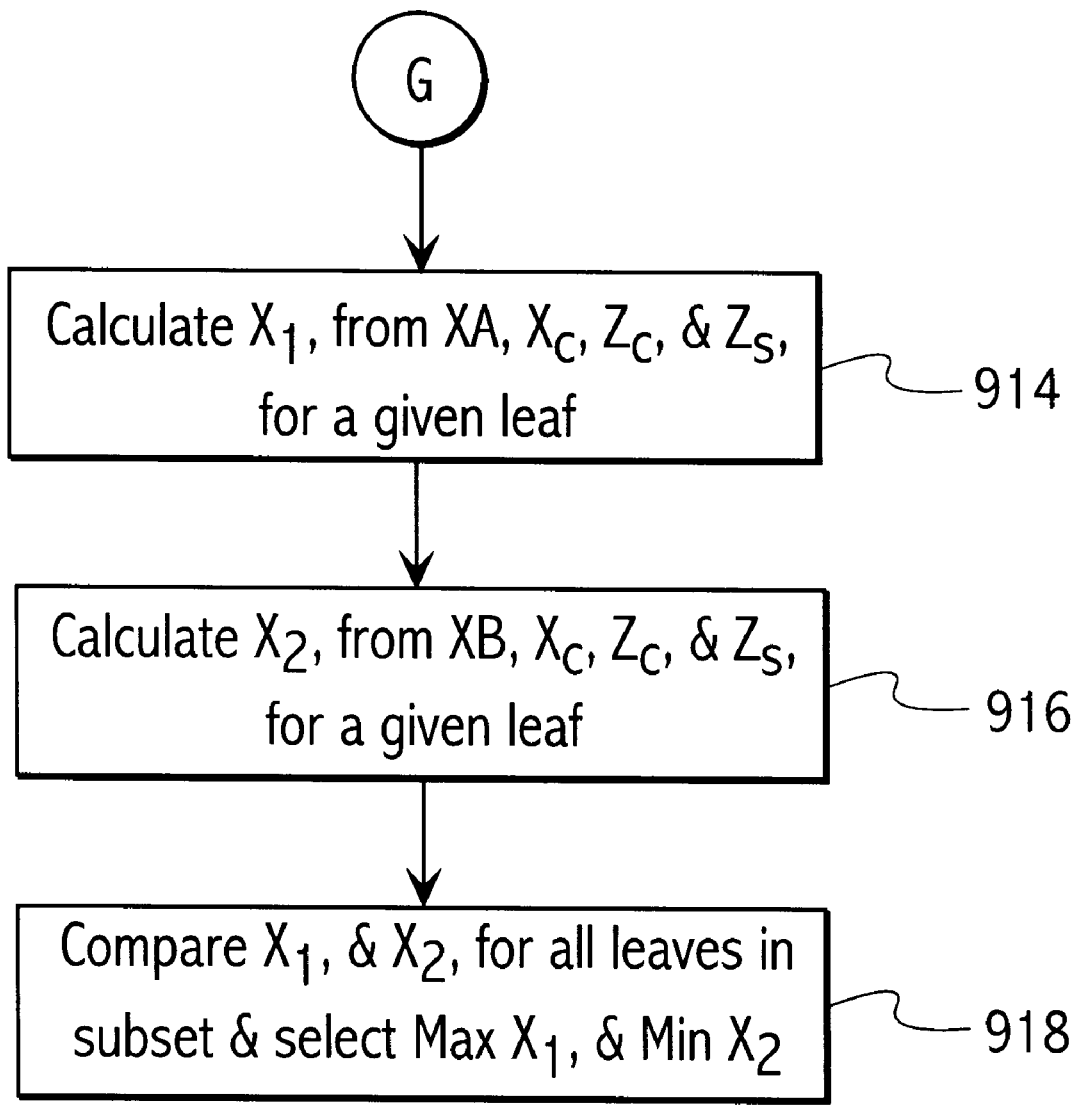

FIG. 17A is a flow diagram of a method according to an embodiment of the present invention for determining the boundaries ($x_1$ and $x_2$) for each collimator leaf in the selected subset and for determining the maximum $x_1$ and the minimum $x_2$ of all the leaves of the subset, such as the determinations of sets 702 and 704 of FIG. 15. The x-values of intersection points are calculated (step 900). Earlier, in steps 414 and 418 of FIG. 10B, and also in the discussion regarding FIG. 13, the y and z values of each intersection point had been determined. Accordingly, an equation may be solved for each leaf to determine the x-values of the intersection points in light of the previously determined y and z values.

For a given leaf and a given z value corresponding to an intersection point with that leaf, the x-value for that intersection point can be determined from the initial specification of the position of that leaf. The initial specification of the position of the leaves should be one of the inputs to the process (as for example, in FIG. 5, the aperture 100 is defined in terms of the leaf positions of the leaves 104). These specified leaf positions are the positions of the edges of shadows cast by the leaves onto the calculation plane from a point source at the target position (such as source 17 of FIG. 8) (These are the projected leaf positions, call the variable $x_p$). Because the edges of the collimator are divergent, the ratio of the x value of the intersection point to $x_p$ is equal to the ratio of the z value of the intersection point to the z value of the calculation plane ($z_c$). Hence:

$$x_i = x_p (z_i / z_c).$$

where $z_i$ is the z value of the intersection point, $z_c$ is 100 cm in the example shown in FIG. 8, $x_i$ is the x value of the intersection point, and $x_p$ is the projected leaf position of the leaf that contains the intersection point being evaluated.

Figure 11:
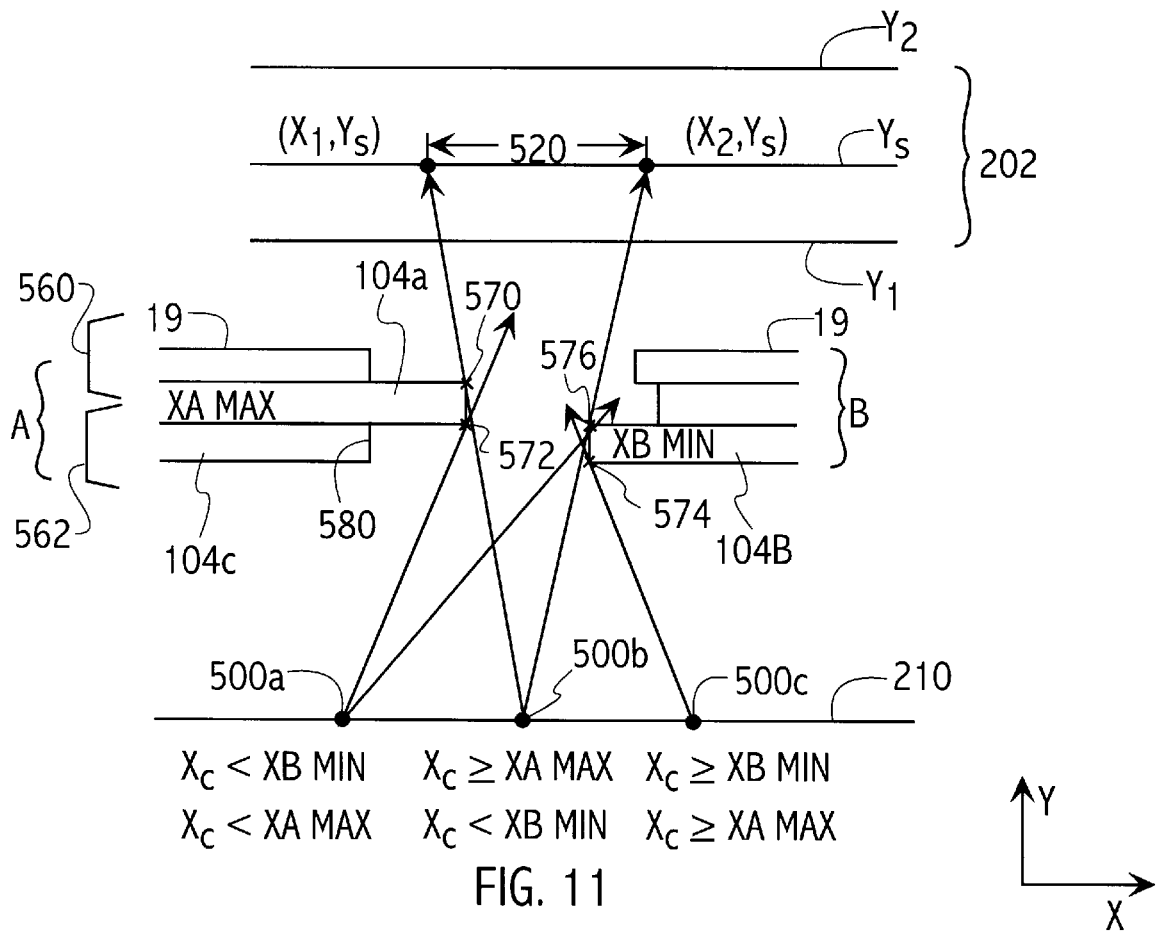
FIGS. 11–13 illustrate various ray tracings through various perspectives of a collimator.
Figure 12:
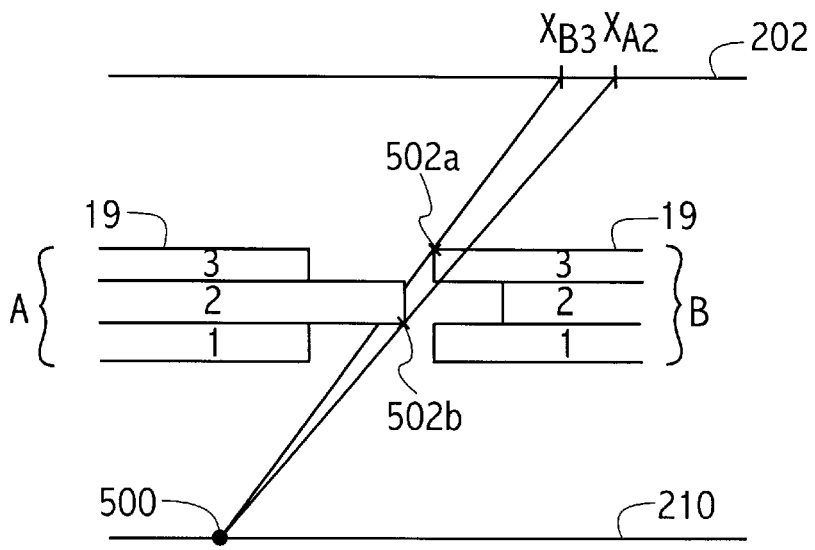

It is then determined whether $x_c$ of the calculation point is less than XAMAX (step 902). In the example shown in FIG. 11, the calculation point 500A is shown to have an $x_c$ less than XAMAX, while calculation points 500B and 500C are shown to have $x_c$ greater than or equal to XAMAX. If the $x_c$ of the current calculation point is not less than XAMAX, then the intersections with the radiation ray and the collimator leaves in the subset of collimator leaves of side "A" (as shown in the example of FIG. 11) are on the edges farther from the calculation point (step 904). For example, in FIG. 11, the calculation points 500B and 500C each have an $x_c$ which is shown to be greater than or equal to XAMAX. Accordingly, a ray traced from calculation points 500B and 500C would intersect an edge that is farther from $y_c$, such as edge 570, of the subset of collimator leaves of side "A".

If $x_c$ of the calculation point is less than XAMAX (step 902), then intersections with the ray and the collimator leaves of the subset of side "A" will be on the edge closer to the calculation point (step 906). For example, in FIG. 11, calculation point 500A is shown to have an $x_c$ less than XAMAX. Accordingly, a ray traced from calculation point 500A to scattering plane 202 intersects the subset of collimator leaves on the edges closer to the calculation point on the leaves on side "A". For example, the ray traced from calculation point 500A is shown to intersect with leaf 104A at the edge closer to the calculation point, such as edge 572.

It then determined whether $x_c$ is less than XBMIN (step 908). In the example shown in FIG. 11, the calculation points 500A and 500B are shown to have an $x_c$ which is less than XBMIN. If $x_c$ is greater than or equal to XBMIN, then the intersections with the ray traced from the calculation point to the scattering plane and the collimator leaves in the subset of side "B" of the collimator will be on the edges closest to the calculation point of the collimator leaves (step 910). For example, in FIG. 11, calculation point 500C is shown to have an $x_c$ greater than or equal to XBMIN. Accordingly, a ray traced from calculation point 500C to the scattering plane 202 intersects leaf 104B on the edge closer to the calculation point, such as edge 574.

If $x_c$ of the calculation point is less than XBMIN, then intersections with a ray traced from the calculation point to the scattering plane and the collimator leaves in the subset of side "B" of the collimator are on the edges farther from the calculation point (step 912). In the example shown in FIG. 11, calculation points 500A and 500B are shown to have $x_c$ less than XBMIN. A ray traced from these calculation points 500A and 500B to the scattering plane 202 is shown to intersect leaf 104B at an edge further from the calculation point, such as edge 576.

$X_1$ is then calculated for a given leaf (step 914). Since XA, $x_c$, $z_c$, and $z_s$ are all known, $x_1$ can be calculated from these known variables. $X_c$ has already been determined in step 420 of FIG. 10B; $z_c$ is a predetermined value, such as 100 cm (as shown in the example of FIG. 8 wherein calculation plane 210 is placed 100 cm below radiation source 17); and $z_s$ is also a predetermined number, such as 10 cm, (such as the $z_s$ shown in FIG. 8, wherein scattering plane 202 is placed 10 cm below radiation source 17).

XA is the x value for the intersection point at the appropriate edge of the given leaf under consideration, for which a value of $X_1$ is to be calculated. In the discussion related to step 900 of FIG. 17A, wherein the x values of the intersection points are calculated, the variable $x_i$ was used as a generic variable. XA is just the $x_i$ for the leaf under consideration on side A of the collimator. Similarly, the z value of that intersection point is required (in the discussion related to step 900 of FIG. 17A, the z value of the intersection point is generically labeled $z_i$, here it is referred to as ZA for consistency when referring to the z value of the leaf under consideration on side A of the collimator). Note that XA is not XAMAX, but XAMAX is related to the XA for the leaf that sticks out the most into the field.

Figure 17C:
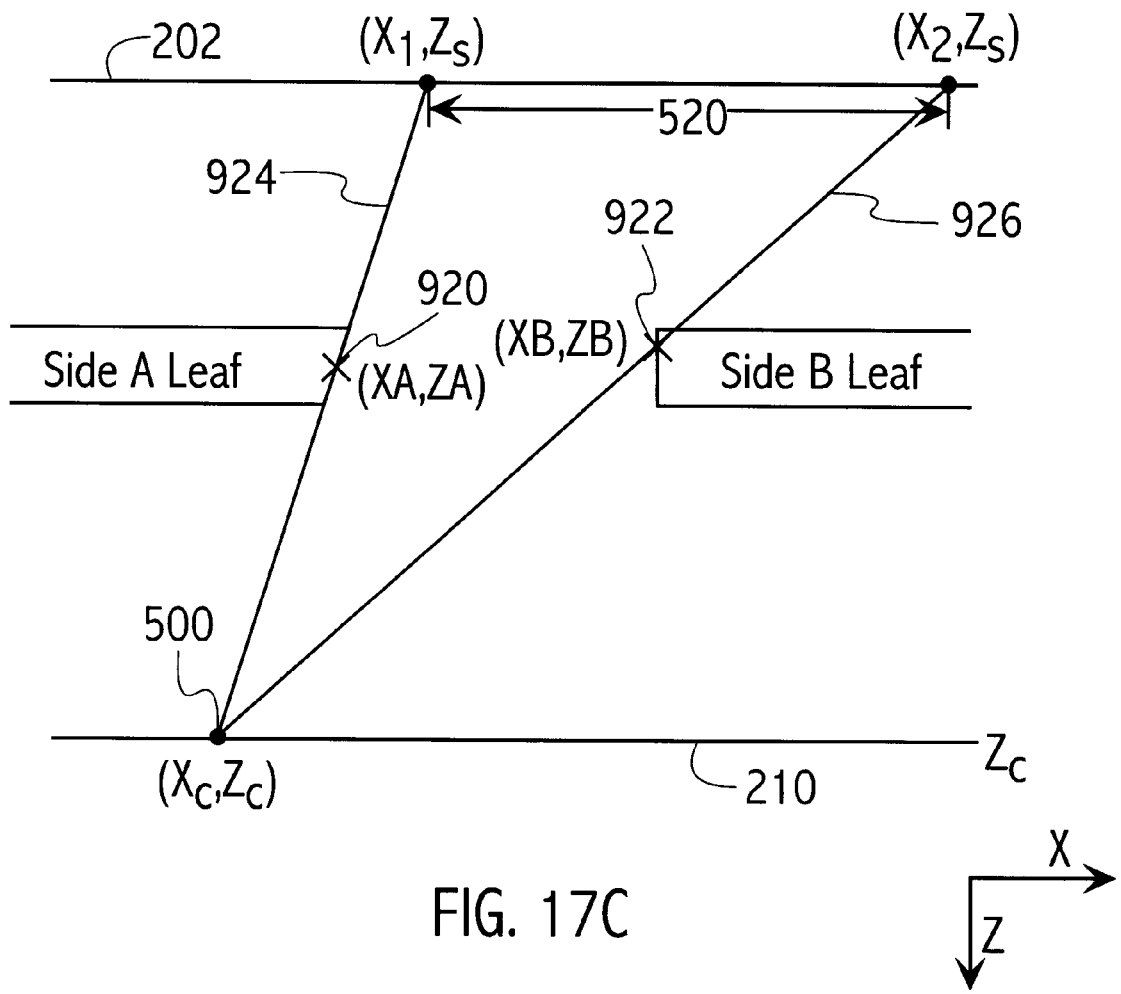
FIG. 17C is an illustration of an example of the method described in conjunction with FIGS. 17A–17B.

As shown in FIG. 17C, since $z_s$, ZA, XA, $z_c$, $x_c$ are all known at this point, $X_1$ can be determined by a linear equation. The points ($x_c$, $z_c$) and (XA,ZA) determine a linear equation, and since the point ($X_1,z_s$) lies on this line, putting $z_s$ into the linear equation allows one to solve for $X_1$. As implied by the example of FIG. 17C, the intersection points 920 and 922 ((XA, ZA) and (XB, ZB)) can be determined by solving for the intersection of the two linear equations that describe the ray being traced (924 and 926) and the edge of the leaf that is being intersected by the ray (e.g. points 504A–504D of FIG. 13). Note that ZA and ZB have previously been determined using the y-z plane view and the projections of these two linear equations onto the y-z plane, while XA and XB have been determined using similar triangles in the x-z plane. Using this information allows us to now solve for $X_1$.

An example of such an equation is as follows:

$$X_1 = XA + (z_s - ZA)(XA - x_c)/(ZA - zc)$$

Many variations of this equation may be used to vary the efficiency of the calculation. For example, a variation such as the following may also be used:

$$X_1 = x_c + d*c$$

where $d = z_s - z_c$ and can be calculated before entering the loops, and only $c = (XA - x_c)/(ZA - z_c)$ is calculated within the loops (not $X_1$ itself) and the value of c that would produce the maximum $X_1$ is used since $X_1$ only has to be calculated for the maximum condition (the one with the maximum value of c). (Note also that $(ZA-z_c)$ can be calculated before entering the loops which vary $x_c$ and save on redundant calculations.)

For the leaves on Side A, a unique value of $X_1$ can be determined for each leaf. That is, any given leaf on side A, if it were to be the only leaf to exist on that side, will block out scattered radiation, and thus it provides an $X_1$ limit on the scattering strip. If a ray was traced from a calculation point to the edge of the leaf (the edge that blocks the most radiation) and onto the scattering plane, $X_1$ would be the leftmost limit of the scattering strip that could contribute to radiation.

For all the leaves in side A, such an $X_1$ could be determined (pretending that each leaf were the only one existing), but only the maximum $X_1$ is needed, and this will be associated with the leaf on side A that blocks the most radiation from the left side of the scattering strip. In many cases this could be the leaf that sticks out furthest into the field, but not always.

The leaves on side A do not have an $X_2$ value associated with them. The reverse is true for the leaves on side B. $X_2$ may then be calculated for each given leaf on side B (step 916). $X_2$ may be calculated from XB, $x_c$, $z_c$ and $z_s$. Each leaf on side B can have an associated $X_2$ value, but only the minimum $X_2$ value is necessary for the calculation. There are no $X_1$ values associated with the leaves on side B. The values $X_1$ and $X_2$ are the limits of the scattering strip, and MIN $X_2$ (the smallest $X_2$ value calculated by pretending that each one of the leaves on side B was the only one that existed) should be greater than MAX $X_1$ (the largest X1 value calculated by pretending that each one of the leaves on side A was the only one that existed) for scatter to be present.

$X_1$ is the x coordinate of the left edge of the scattering strip, and $X_2$ is the x coordinate of the right edge of the scattering strip. However, if a given leaf on side A were the only one to exist, it would determine $X_1$, and if a given leaf on side B were the only one to exist, it would determine $X_2$. Since there are many leaves on both side A and side B, the leaves that block the most radiation is desired to set the $X_1$ and $X_2$ properties of the scattering strip.

The $x_1$ and $x_2$ are then compared for all the leaves in the subset, and a maximum $x_1$ and a minimum $x_2$ are selected (step 918). Since it is desirable to have the $X_1$ property of the scattering strip to be from the leaf that blocks the most radiation on side A, the leaf that produces the maximum $X_1$ value among all the leaves on side A is selected. That maximum $X_1$ is now used to set the x coordinate of the left edge of the scatter strip. A similar process occurs for the leaves on side B and $X_2$, except that the minimum $X_2$ is needed, since the leaf on side B that has the minimum $X_2$ is the leaf that blocks the most radiation from the scatter strip and should be what is used to set the x coordinate of the right edge of the scattering strip. If the x coordinate of the left edge of the scattering strip is greater than or equal to the x coordinate of the right edge of the scattering strip, then no scattered radiation can come from that scatter strip and contribute fluence to the calculation point under consideration.

Figure 18:
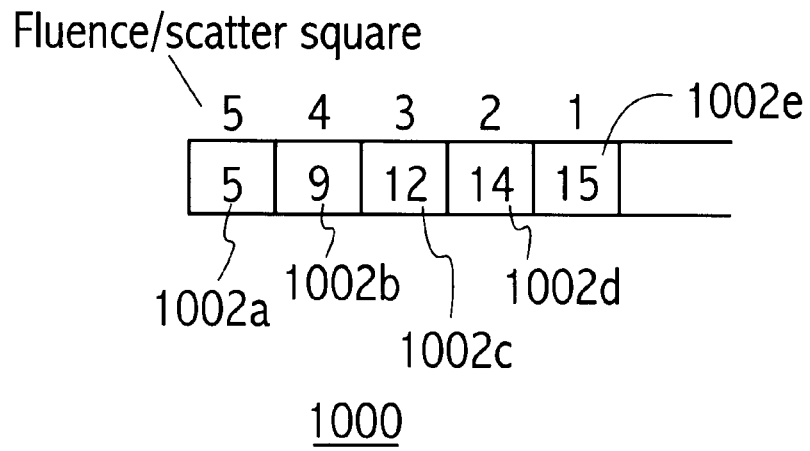
FIG. 18 is an illustration of a pre-calculated strip according to an embodiment of the present invention.

FIG. 18 is an illustration of pre-integrated values of a scatter strip lookup table. Each position in the scatter strip lookup table corresponds to a square in a scatter strip of the scattering plane. Within each memory location of the lookup table scatter strip 1000, a cumulative value indicating the fluence per scatter square is stored. For example, location 1002A of the scatter strip lookup table is shown to have five fluence per scatter square. If location 1002B of the lookup table scatter strip 1000 corresponds to a square in the scattering plane which has four fluence per scatter square, then the value stored in location 1002B would be nine (5+4), since the stored values are cumulative from the previous squares. Likewise, location 1002C of the lookup table scatter strip 1000 is shown to store the value 12, assuming that location 1002C is associated with a square on the scattering plane which corresponds to three fluence per scatter square (3+4+5).

Figure 19:
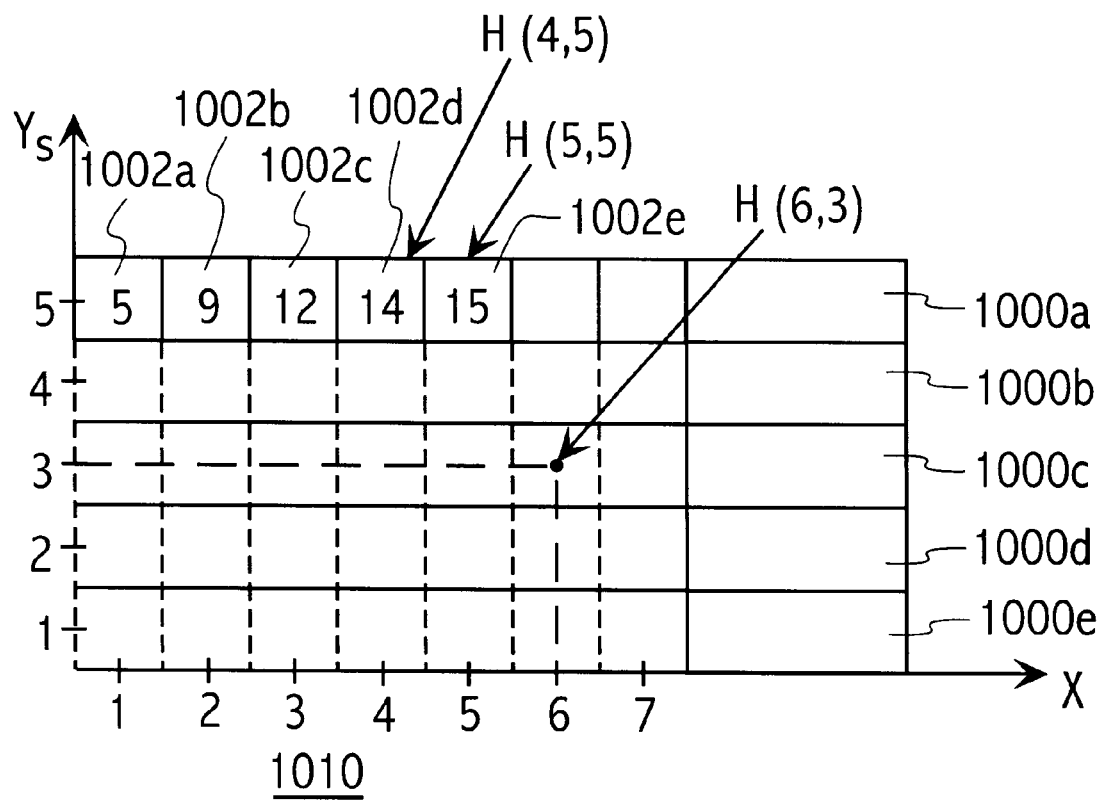
FIG. 19 is a conceptual illustration of a lookup table of pre-calculated strips according to an embodiment of the present invention.

FIG. 19 shows an example of a scatter strip lookup table 1010 which includes multiple strips 1000A–1000E. The number of reserved values for x and reserved values for y for the lookup table 1010 depends on the geometry of the system. For example, 90 values for x may be reserved and 56 values for y may be reserved. Examples of an amount of memory reserved for each value include approximately 4 bytes, or approximately 8 bytes, depending on implementation preferences.

A particular x and y of a scatter strip on the scattering plane associated with a particular calculation point may be looked up in the lookup table 1010 by looking up $H(x, y_s)$, wherein H is the position of the lookup table wherein the desired information relating to x and $y_s$ may be found. For example, if the scatter strip 520 shown in FIG. 11 has an $x_1$=−3 mm, $x_2$=4 mm, and $y_s$=5 mm, then step 308 of FIG. 9 and step 432 of FIG. 10C would lookup a value in the lookup table 1010 of FIG. 19 by searching for H(4, 5) which may be found by looking up the fifth strip 1000A (corresponding to $y_s$=5), and looking up the fourth position 1002D of the fifth strip 1000A. The fourth position 1002D is counted from the first position 1002A up to the fourth position 1002D. As previously discussed, the value associated with the fourth position 1002D of the fifth strip 1000A is a cumulative value which includes the fluence per scatter square for all of the scatter squares within the scatter strip with an x value less than the looked up x value. For example, in the position 1002D, the value 14 is the cumulative value which includes all the fluence per scatter square value associated with each of the scatter squares in the scatter strip which correspond to the previous positions 1002A–1002C. As shown in the example of FIG. 18, if the fluence per scatter square associated with the squares of the scatter strip which is being analyzed and which correspond to the lookup table locations 1002A–1002E are 5, 4, 3, 2, and 1, respectively, then the cumulative value of the fourth location 1002D would be 14 (5+4+3+2).

Additionally, since $x_1$=−3 in this example, H(3, 5) is also looked up. When an x value is negative, the lookup function looks up the absolute value of x. Accordingly, the third location 1002C of the fifth strip 1000A is looked up. The value associated with the third position 1002C of the fifth strip 1000A is 12 in this example. In this example, the previous $H(x_2, y_s)$ result is then added to the current result of $H(x_1, y_s)$ Accordingly, the fluence value of this scatter strip ($y_s$=5 mm, $x_1$=−3 mm, $x_2$=4 mm) would be 26 ($H(x_2, y_s)$+$H(x_1, y_s)$=12+14=26).

Figure 20:
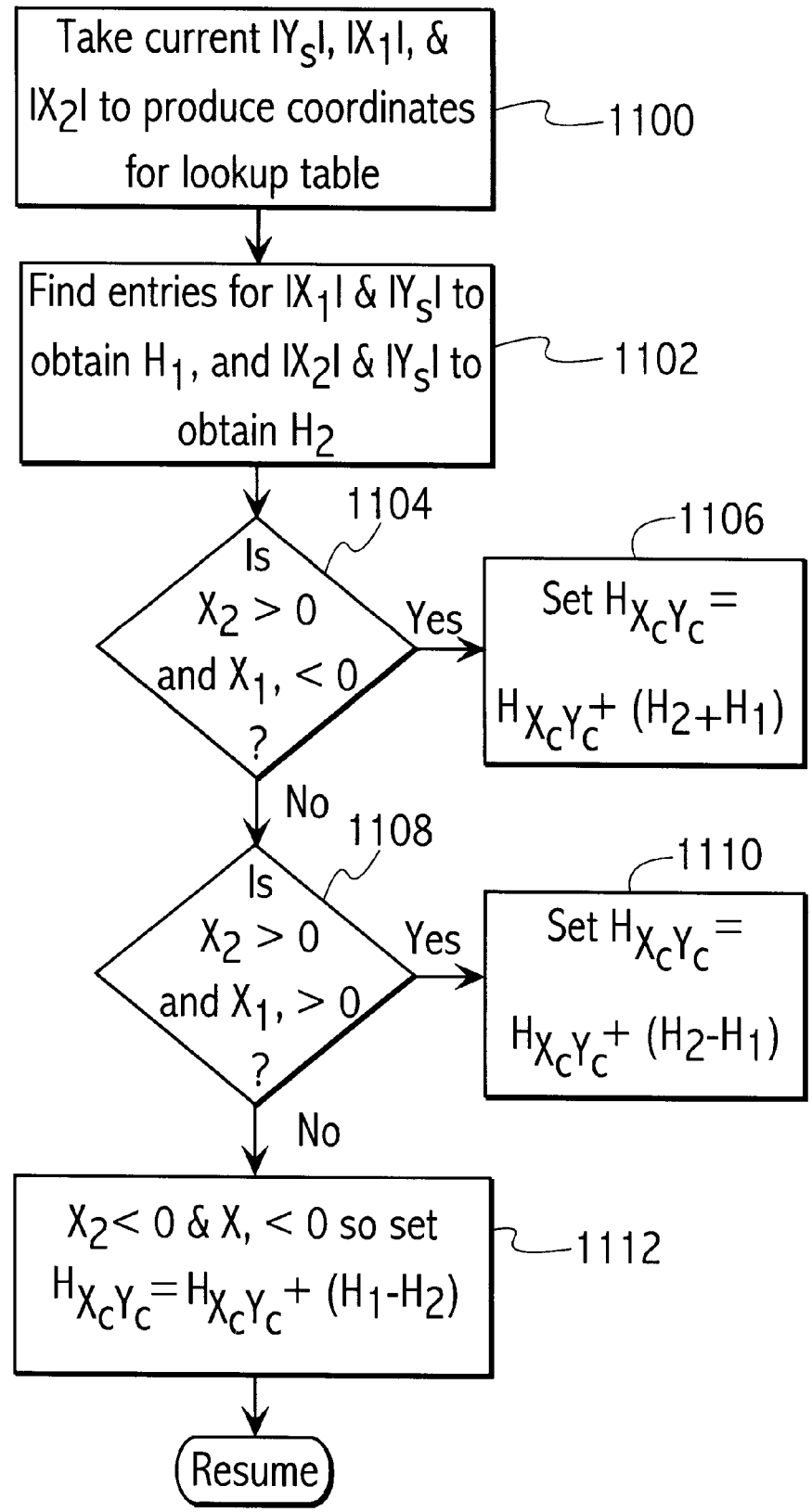
FIG. 20 is a flow diagram of a method according to an embodiment of the present invention for determining a scatter contribution to the fluence of a point on the calculation plane.

FIG. 20 is a flow diagram of a method according to an embodiment of the present invention for determining the scatter contribution to fluence by using a lookup table. For example, this method may be used in looking up pre-integrated values of the scatter strip lookup table to perform the fluence calculation as stated in steps 432 of FIG. 10C and 308 of FIG. 9.

Absolute values of the current $y_s$, $x_1$, and $x_2$ are used to produce coordinates for the lookup table (step 1100). As previously mentioned in conjunction with FIG. 19, these absolute values are used for $H(x_1, y_s)$ and $H(x_2, y_s)$. Entries for the absolute values of $x_1$ and $y_s$ are found to obtain $H_1$ and absolute values of $x_2$ and $y_s$ are used to obtain H2 (step 1102). It is then determined whether $x_2$ is greater than 0 and $x_1$ is less than 0 (step 1104). If $x_2$ is greater than 0 and $x_1$ is less than 0, then the fluence of the calculation point on the calculation plane is added to $H_2+H_1$ (set $H(x_c, y_c)=H(x_c, y_c)+(H_2+H_1)$) (step 1106).

If $x_2$ is not greater than 0 or $x_1$ is not less than 0, then it is determined whether $x_2$ is greater than 0 and $x_1$ is greater than 0 (step 1108). If $x_2$ is greater than 0 and $x_1$ is greater than 0, then the fluence is set equal to the current fluence plus $H_2-H_1$ (set $H(x_c, y_c)=H(x_c, Y_c)+(H_2-H_1)$)(step 1110).

If $x_2$ is not greater than 0 or $x_1$ is not greater than 0, then it is assumed $x_2$ is less than 0 and $x_1$ is less than 0, so the fluence is set equal to the current fluence plus $H_1-H_2$ (set $H(x_c, y_c)=H(x_c, y_c)+(H_1-H_2)$) (step 1112). Thereafter, the flow diagrams of FIG. 9 and FIG. 10C are resumed such that step 312 of FIG. 9 and step 434 FIG. 10C are determined.

The formula for creating the entries of the pre-integrated values is shown in FIG. 18. (i.e. FIG. 18 shows the cumulative values, where the result for a given entry is the sum of the previous entry and the individual fluence value for the square of the current entry.) The actual value of the fluence for the individual squares of the scattering plane (i.e. instead of the values 5, 4, 3, 2, and 1) are generated from $Ae^{-br}$ where the values of A and b are properties of the beam and can be determined by fitting experimental values of head scatter (radiation scatter) factors to calculated values of head scatter factors. This fitting process can be done with standard techniques for curve fitting that one can find in a numerical recipes book (e.g. "Numerical Recipes in C" by Press, Teukolsky, Vetterling and Flannery, 1992, Cambridge University Press.) Also, the paper: *Head Scatter Modeling for Irregular Field Shaping and Beam Intensity Modulation*, by Hounsell & Wilkinson, PHYS. MED. BIOL. 42 (1997) 1739–1747, IOP Publishing Ltd., describes the process of determining these parameters A and b.

The formulas are actually recursion relations: $H(x_s, y_s)=H(x_s-1,y_s)+Ae^{-br}$, where $r=(x_s^2+y_s^2)^{1/2}$. This gives a crude approximation, a more useful formula that allows one to use the table to perform interpolation would be given by $H(x_s, y_s)=H(x_s-1,y_s)+A(e^{-bu}+e^{-bv})/2$, where $u=(x_s^2+y_s^2)^{1/2}$ and $v=((x_s-1)^2 y_s^2)^{1/2}$, and the starting value for the recursion series is $H(0,y_s)=0$, since a strip of zero length has no contribution to the scatter at all. In this formula, $x_s$ only takes on positive integer values and $y_s$ only needs to be positive values. (Hence the choice of mm as the unit for the dimensions in the scattering plane.) Because of the radial symmetry of the problem, the stored table only needs to be done for the first quadrant ($x_s>0$ and $y_s>0$). Also, because one can interpolate with this table, and it is clear that the value for a zero length strip is zero, the table does not need to store values for $x_s=0$, so the table stores values only for $y_s=0$, 1, 2 . . . $y_s$Max and xs=1, 2, 3, . . . $x_s$Max. $x_s$Max and $y_s$Max would be the maximum index for columns and rows, respectively, and are determined by the geometry of the collimator and the location of the scattering plane, in terms of the maximum visible area of the scattering plane that would be visible from the calculation points that are furthest away from isocenter in the calculation plane. This can be simply determined using similar triangles.

Figure 21:
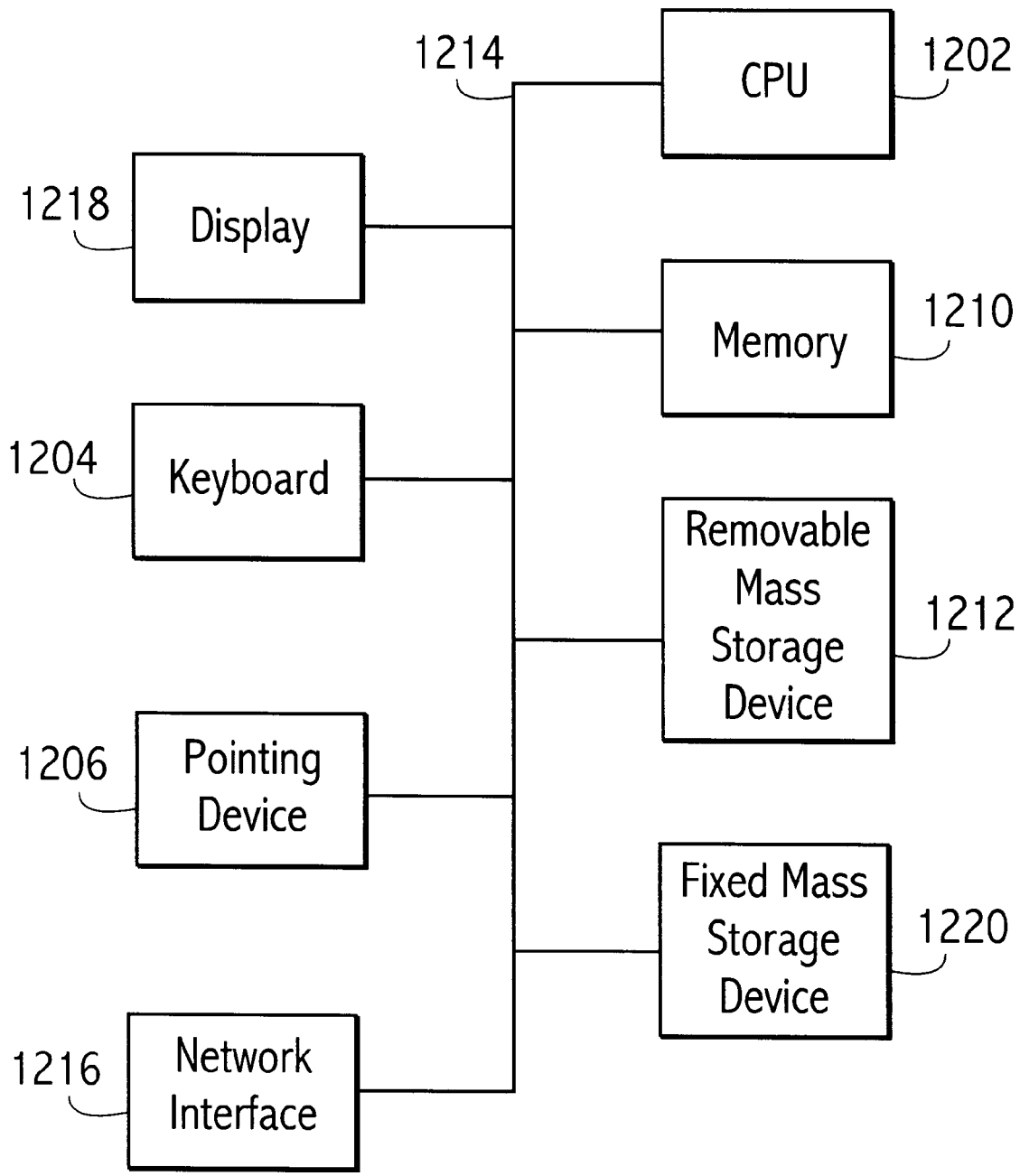
FIG. 21 is a block diagram of a computer suitable for implementing an embodiment of the present invention.

FIG. 21 is a block diagram of a general purpose computer system 1200 suitable for carrying out the processing in accordance with one embodiment of the present invention. FIG. 21 illustrates one embodiment of a general purpose computer system. Other computer system architectures and configurations can be used for carrying out the processing of the present invention. Computer system 1200, made up of various subsystems described below, includes at least one microprocessor subsystem (also referred to as a central processing unit, or CPU) 1202. That is, CPU 1202 can be implemented by a single-chip processor or by multiple processors. CPU 1202 is a general purpose digital processor which controls the operation of the computer system 1200. Using instructions retrieved from memory 1210, the CPU 1202 controls the reception and manipulation of input data, and the output and display of data on output devices.

CPU 1202 is coupled bi-directionally with memory 1210 which can include a first primary storage, typically a random access memory (RAM), and a second primary storage area, typically a read-only memory (ROM). As is well known in the art, primary storage can be used as a general storage area and as scratch-pad memory, and can also be used to store input data and processed data. It can also store programming instructions and data, in the form of data objects and text objects, in addition to other data and instructions for processes operating on CPU 1202. Also as well known in the art, primary storage typically includes basic operating instructions, program code, data and objects used by the CPU 1202 to perform its functions. Primary storage devices 1210 may include any suitable computer-readable storage media, described below, depending on whether, for example, data access needs to be bi-directional or uni-directional. CPU 1202 can also directly and very rapidly retrieve and store frequently needed data in a cache memory (not shown).

A removable mass storage device 1212 provides additional data storage capacity for the computer system 1200, and is coupled either bi-directionally or uni-directionally to CPU 1202. For example, a specific removable mass storage device commonly known as a CD-ROM typically passes data uni-directionally to the CPU 1202, whereas a floppy disk can pass data bi-directionally to the CPU 1202. Storage 1212 may also include computer-readable media such as magnetic tape, flash memory, signals embodied on a carrier wave, PC-CARDS, portable mass storage devices, holographic storage devices, and other storage devices. A fixed mass storage 1220 can also provide additional data storage capacity. The most common example of mass storage 1220 is a hard disk drive. Mass storage 1212, 1220 generally store additional programming instructions, data, and the like that typically are not in active use by the CPU 1202. It will be appreciated that the information retained within mass storage 1212, 1220 may be incorporated, if needed, in standard fashion as part of primary storage 1210 (e.g. RAM) as virtual memory.

In addition to providing CPU 1202 access to storage subsystems, bus 1214 can be used to provide access other subsystems and devices as well. In the described embodiment, these can include a display monitor 1218, a network interface 1216, a keyboard 1204, and a pointing device 1206, as well as an auxiliary input/output device interface, a sound card, speakers, and other subsystems as needed. The pointing device 1206 may be a mouse, stylus, track ball, or tablet, and is useful for interacting with a graphical user interface.

The network interface 1216 allows CPU 1202 to be coupled to another computer, computer network, or telecommunications network using a network connection as shown. Through the network interface 1216, it is contemplated that the CPU 1202 might receive information, e.g., data objects or program instructions, from another network, or might output information to another network in the course of performing the above-described method steps. Information, often represented as a sequence of instructions to be executed on a CPU, may be received from and outputted to another network, for example, in the form of a computer data signal embodied in a carrier wave. An interface card or similar device and appropriate software implemented by CPU 1202 can be used to connect the computer system 1200 to an external network and transfer data according to standard protocols. That is, method embodiments of the present invention may execute solely upon CPU 1202, or may be performed across a network such as the Internet, intranet networks, or local area networks, in conjunction with a remote CPU that shares a portion of the processing. Additional mass storage devices (not shown) may also be connected to CPU 1202 through network interface 1216.

An auxiliary I/O device interface (not shown) can be used in conjunction with computer system 1200. The auxiliary I/O device interface can include general and customized interfaces that allow the CPU 1202 to send and, more typically, receive data from other devices such as microphones, touch-sensitive displays, transducer card readers, tape readers, voice or handwriting recognizers, biometrics readers, cameras, portable mass storage devices, and other computers.

In addition, embodiments of the present invention further relate to computer storage products with a computer readable medium that contain program code for performing various computer-implemented operations. The computer-readable medium is any data storage device that can store data which can thereafter be read by a computer system. The media and program code may be those specially designed and constructed for the purposes of the present invention, or they may be of the kind well known to those of ordinary skill in the computer software arts. Examples of computer-readable media include, but are not limited to, all the media mentioned above: magnetic media such as hard disks, floppy disks, and magnetic tape; optical media such as CD-ROM disks; magneto-optical media such as floptical disks; and specially configured hardware devices such as application-specific integrated circuits (ASICs), programmable logic devices (PLDs), and ROM and RAM devices. The computer-readable medium can also be distributed as a data signal embodied in a carrier wave over a network of coupled computer systems so that the computer-readable code is stored and executed in a distributed fashion. Examples of program code include both machine code, as produced, for example, by a compiler, or files containing higher level code that may be executed using an interpreter.

The computer system shown in FIG. 21 is but an example of a computer system suitable for use with the invention. Other computer systems suitable for use with the invention may include additional or fewer subsystems. In addition, bus 1214 is illustrative of any interconnection scheme serving to link the subsystems. Other computer architectures having different configurations of subsystems may also be utilized.

An example of an implementation of an embodiment of the present invention is as follows:

---

(Note that the set of segments resulting from the segmentation routine is the input to this code; this includes the map of primary beam locations and the positions of all leaves and jaws for each segment.)

| | |
|---|---|
| 1 | Precalculate scattering strip integrals and store in a table |
| 2 | Precalculate line of sight coefficients |
| 3 | Precalculate y coordinates of calculation points for the points in the intensity map |
| 4 | Precalculate y coordinates of projected leaf edges at the calculation plane |
| 5 | Precalculate y coordinates of leaf edges at the leaf top plane |
| 6 | Precalculate y coordinates of leaf edges at the leaf bottom plane |
| 7 | Initialize head scatter factor (to primary for cells under beam or 0 otherwise) |
| 8 | Precalculate x coordinates of calculation points for the points in the intensity map |
| 9 | For each segment |
| 10 |    Determine the number of closed polygons (called groups in the code) in the segment |
| 11 |    Determine the first and last y coordinates that bound the group |
| 12 |    Determine y coordinates of jaw y1 at top of jaw and bottom of corresponding leaf |
| 13 |    Determine y coordinates of jaw y2 at top of jaw and bottom of corresponding leaf |
| 14 |    For each $y_c$ (this calculation row is parallel to the scattering strips) |
| 15 |       Determine the $y_s^{jmin}$ and $y_s^{jmax}$ values of $y_s$, (first and last strips seen through jaws) |
| 16 |       if $y_s^{jmax} > y_s^{jmin}$ (i.e. continue only if jaws don't obscure scatter) |
| 17 |          For each group |
| 18 |             Determine $y_s^{gmin}$ and $y_s^{gmax}$ values of $y_s$, (1st & last strips seen through area bounded by 1st and last open leaves of group) |
| 19 |             Determine $y_s^{min} = \mathrm{Max}(y_s^{jmin}, y_s^{gmin})$ and $y_s^{max} = \mathrm{Min}(y_s^{jmax}, y_s^{gmax})$ (limits of visible strips, set interpolation in y here) |
| 20 |             For each $y_s$ in $[y_s^{min}, y_s^{max}]$ (the loop will not occur if $y_s^{max} < y_s^{min}$, i.e. if scatter is blocked by leaves) |
| 21a |                Split each ray into sub-rays that intersect exactly one leaf at the top and exactly one leaf at the bottom |
| 21b |                For each sub-ray, do the following: |
| 21c |                   Determine the subset of leaves that contain the yz sub-ray from the line $y = y_c$ to the line $y = y_{se}$ (leaf rows $r_b$ to $r_t$) |
| 21 |                   ($r_b$ is the leaf row corresponding to where the ray hits the bottom leaf plane, $r_t$ is for the top leaf plane) |
| 22 |                   (note that row order increases as y coordinate decreases, and note that the effective $y_s = Y_{se}$ must be used.) |
| 24 |                   If there is more than one leaf in the subset |
| 25 |                      For each leaf in the subset |
| 26 |                         Determine the scaled vertical positions (z) of the intersection between the yz ray and the yz projected leaf edges |
| 27 |                      Next leaf |
| 28 |                      For each leaf in the subset |

-continued

| | |
|---|---|
| 29 | Determine the x coordinates of the intersection between the yz ray and the yz projected leaf edges |
| 30 | Determine the z coordinates of these intersection points using the calculation plane as z=0 |
| 31 | Next leaf |
| 32 | Determine the positions of the leaves in the subset that are furthest into the field ($x_1^{max}$ and $x_2^{min}$) |
| 33 | Determine the rows of the first and last leaf (in row order) with the $x_1^{max}$ position (x1MaxRLo and x1MaxRHi) |
| 34 | Determine the rows of the first and last leaf (in row order) with the $x_2^{min}$ position (x2MinRLo and x2MinRHi) |
| 35 | End if more than one leaf in subset |
| 36 | For each $x_c$ along the line $y = y_c$ |
| 37 | (Note that all dz1, dzu, dx12, etc are all relative to the calculation plane; u is for upper edge, l is for lower edge |
| 38 | 1 is for leaves in bank 1 (the left bank) and 2 is for leaves in bank 2) |
| 39 | If rb > rt then |
| 40 | If ($x_c$ >= $x_2^{min}$) then for leaves in rows (x2MinRHi, rb) determine the max cotangent dx12/dz1 |
| 41 | Else for leaves in rows (rt, x2MinRLo) determine the max cotangent dxu2/dzu |
| 42 | End if (condition on $x_2^{min}$) |
| 43 | If ($x_c$ >= $x_1^{max}$) then for leaves in rows (rt, x1MaxRLo) determine the min cotangent dxu1/dzu |
| 44 | Else for leaves in rows (x1MaxRhi, rb) determine the min cotangent dx11/dz1 |
| 45 | End if (condition on x1max) |
| 46 | End if (condition on rb, rt) |
| 47 | If rb < rt then |
| 48 | If ($x_c$ < x2min) then for leaves in rows (x2MinRHi, rt) determine the max cotangent dx12/dz1 |
| 49 | Else for leaves in rows (rb, x2MinRLo) determine the max cotangent dxu2/dzu |
| 50 | End if (condition on x2min) |
| 51 | If ($x_c$ < x1max) then for leaves in rows (rb, x1MaxRLo) determine the min cotangent dxu1/dzu |
| 52 | Else for leaves in rows (x1MaxRhi, rt) determine the min cotangent dx11/dz1 |
| 53 | End if (condition on x1max) |
| 54 | End if (condition on rb, rt) |
| 55 | If rb = rt determine $x_R$ and $x_L$ from linear equations in xz plane |
| 56 | If rb <> rt calculate $x_R$ from the max cotangent and $x_L$ from the min cotangent |
| 57 | If $x_R$ > $x_L$ increment head scatter factor for ith segment $S_i(x_c, y_c)$ by $Sgn(x_R)*H(x_R,y_s) - Sgn(x_L)*H(x_L, y_s)$ |
| 58 | (H is the scattering strip integral look up table, note that interpolations in x and y have to be done) |
| 59 | Next xc |
| 60a | Next sub-ray |
| 60b | Next ys |
| 61 | Next group |
| 62 | End if (jaws don't obscure scatter) |
| 63 | Next yc |
| 64 | Next segment |

Correction for Round-off Resulting from Fan-shape of Ray

Figure 22:
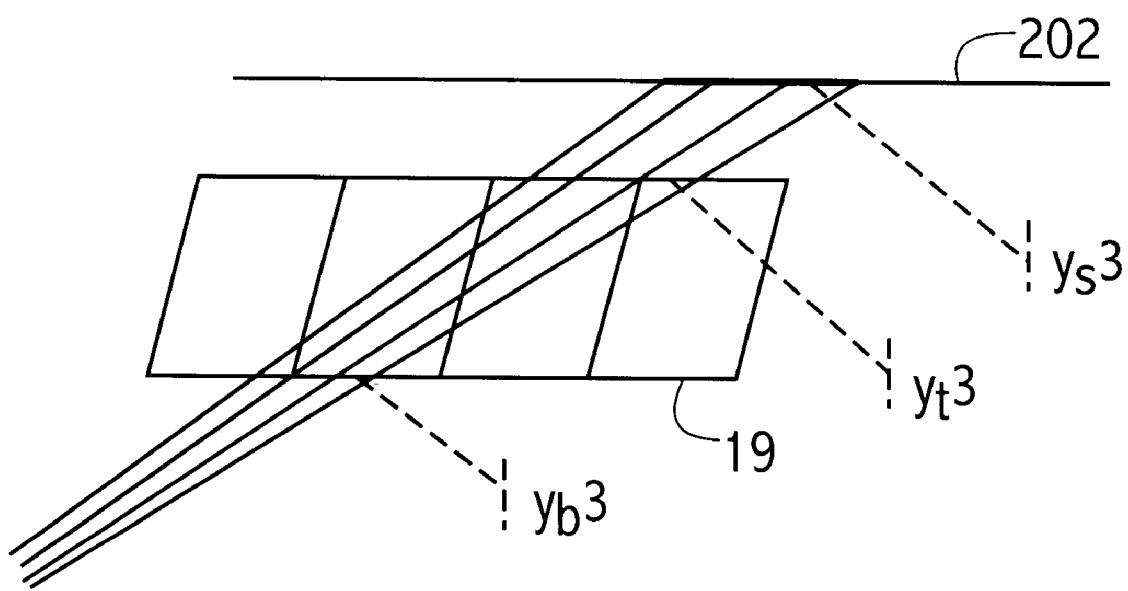
FIG. 22 is an illustration of a correction for round-off resulting from fan-shape of rays.

Referring to FIG. 22, note that if the rays are split into sub-rays to avoid round off error as shown in FIG. 22, the fraction of the scattering strip seen by the sub-ray has to be multiplied to the result for ΔH. FIG. 22 shows the original ray being split into three sub-beams. The original ray has a fan-like shape, originating from the calculation point, flaring out as it goes towards the scattering plane, with the end of the ray covering the width of one scattering strip. Knowing the geometry of the multi-leaf collimator, yc and ys, the fraction of the scattering strip that each sub-ray covers can be calculated using similar triangles. The values of yt and yb then have to be calculated for each sub ray, so instead of using ys determined for the loop, an effective ys is assigned to each ray, but only for the calculation of yt and yb; other parts of the code using ys do not use this effective ys. The effective ys for a given sub-beam would then be equal to the y coordinate of the midpoint of the segment of the scattering strip that the sub-ray spans. This can be seen for the 3$^{rd}$ sub-ray in the figure above, for the point labeled ys3. In the case where the sub-rays are used, the values for dys (the interpolation factor in the y direction) that were calculated for the original ray are replaced by the fraction seen by each sub-ray.

A method and system for calculating scatter radiation has been disclosed. Software written according to the present invention may be stored in some form of computer-readable medium, such as memory or CD-ROM, or transmitted over a network, and executed by a processor.

Although the present invention has been described in accordance with the embodiment shown, one of ordinary skill in the art will readily recognize that there could be variations to the embodiment and these variations would be within the spirit and scope of the present invention. Accordingly, many modifications may be made by one of ordinary skill in the art without departing from the spirit and scope of the appended claims.

What is claimed is :

1. A method for calculating scatter radiation, the method comprising:

provide a collimator leaf position;

determining a subset of collimator leaves; and calculating fluence, wherein the fluence calculation is related to the subset of collimator leaves.

2. The method of claim 1, wherein the collimator leaf position includes the identity of a leaf that is farthest out in a radiation field.

3. The method of claim 1, wherein the subset is associated with a calculation point.

4. The method of claim 3, wherein, when the calculation point is in a first position relative to a first leaf, the subset includes collimator leaves starting from the first leaf to a second leaf, wherein the first leaf is furthest out in a radiation field and the second leaf would be a last leaf traversed by a ray from a calculation point to a scattering plane.

5. The method of claim 3, wherein, when the calculation point is in a second position relative to a first leaf, the subset includes collimator leaves starting from a third leaf to the first leaf, wherein the first leaf is furthest out in a radiation field and the third leaf would be traversed first by a ray from a calculation point to a scattering plane.

6. The method of claim 1, further comprising determining a scatter strip on a scattering plane.

7. The method of claim 6, wherein a predetermined value associated with the scatter strip may be looked up.

8. The method of claim 6, wherein the predetermined value is a cumulative value.

9. The method of claim 6, further comprising determining whether a ray traced from a calculation point to the scatter strip intersects a first portion of a collimator leaf that is closer to the calculation point or a second portion of the collimator leaf that is farther from the calculation point.

10. A system for calculating scatter radiation, the system comprising:

means for providing a collimator leaf position;

means for determining a subset of collimator leaves; and means for calculating fluence, wherein the fluence calculation is related to the subset of collimator leaves.

11. The system of claim 10, wherein the subset is associated with a calculation point.

12. The system of claim 11, wherein, when the calculation point is in a first position relative to a first leaf, the subset includes collimator leaves starting from the first leaf to a second leaf, wherein the first leaf is furthest out in a radiation field and the second leaf would be a last leaf traversed by a ray from a calculation point to a scattering plane.

13. The system of claim 11, wherein, when the calculation point is in a second position relative to a first leaf, the subset includes collimator leaves starting from a third leaf to the first leaf, wherein the first leaf is furthest out in a radiation field and the third leaf would be traversed first by a ray from a calculation point to a scattering plane.

14. A system for calculating scatter radiation comprising:

a memory configured to provide a collimator leaf position;

a processor coupled to the memory, the processor being configured to determine a subset of collimator leaves and also configured to calculate fluence, wherein the fluence calculation is related to the subset of collimator leaves.

15. The system of claim 14, wherein the subset is associated with a calculation point.

16. The system of claim 15, wherein, when the calculation point is in a first position relative to a first leaf, the subset includes collimator leaves starting from the first leaf to a second leaf, wherein the first leaf is furthest out in a radiation field and the second leaf would be a last leaf traversed by a ray from a calculation point to a scattering plane.

17. The system of claim 15, wherein, when the calculation point is in a second position relative to a first leaf, the subset includes collimator leaves starting from a third leaf to the first leaf, wherein the first leaf is furthest out in a radiation field and the third leaf would be traversed first by a ray from a calculation point to a scattering plane.

18. A computer program product for calculating scatter radiation, comprising:

computer code providing a collimator leaf position;

computer code determining a subset of collimator leaves;

computer code calculating fluence, wherein the fluence calculation is related to the subset of collimator leaves; and a computer readable medium that stores the computer codes.

19. The computer program product of claim 18, wherein the computer readable medium is selected from the group consisting of CD-ROM, floppy disk, tape, flash memory, system memory, hard drive, and data signal embodied in a carrier wave.

* * * * *